United States Patent [19]

Mobley et al.

[11] Patent Number: 5,134,121
[45] Date of Patent: Jul. 28, 1992

[54] NERVE GROWTH FACTOR PEPTIDES

[75] Inventors: William C. Mobley, Moraga; Frank M. Longo, San Francisco, both of Calif.; James C. Kauer, Kennett Square, Pa.

[73] Assignee: Regents of the University of California, Berkeley, Calif.

[21] Appl. No.: 640,577

[22] Filed: Jan. 14, 1991

Related U.S. Application Data

[63] Continuation of Ser. No. 299,698, Jan. 23, 1989, abandoned, which is a continuation-in-part of Ser. No. 173,975, Mar. 28, 1988, abandoned.

[51] Int. Cl.$^5$ .................... C07K 7/06; C07K 7/08; A61K 37/02
[52] U.S. Cl. ........................... 514/14; 514/15; 514/16; 514/17; 514/18; 530/326; 530/327; 530/328; 530/329; 530/330; 530/839; 930/120; 930/DIG. 800
[58] Field of Search ............. 514/12, 13, 14, 15, 514/16, 17, 18; 530/324, 325, 326, 327, 328, 329, 330, 839; 930/120, DIG. 800

[56] References Cited

U.S. PATENT DOCUMENTS 3,842,067 10/1974 Sarantakis et al. .
3,862,925 1/1975 Sarantakis et al. .
4,626,523 12/1986 Vale, Jr. et al. .
4,666,829 5/1987 Glenner et al. .

FOREIGN PATENT DOCUMENTS 0121338 10/1984 European Pat. Off. .

OTHER PUBLICATIONS

Dayoff et al., *Atlas of Protein Sequence and Structure*, vol. 5:89-99, 1972.
Yanker, B. A. et al., Ann. Rev. Biochem., 51:845-868, 1982.
Ullrich, Axel et al., Nature, 303:821-825, Jun. 1983.
Sabesan, M. N., J. Theor. Biol., 83:469-476, 1983.
Creighton, *Proteins*, W. H. Freeman & Co., p. 366, 1984.
Chang, et al., J. Pharmacol. Exp. Ther., 227:403-408.
Hardy, et al., J. Med. Chem., 32:1108-1118 (1989).
Hazum, Trends Pharmacol. Sci., pp. 454-456 (Nov. 1983).
Jacobson, et al., J. Med. Chem. 32:1708-1717 (1988).
Liesi, et al., FEBS Letters, 244:141-148 (1989).
Pikkarinen, et al., J. Biol. Chem., 263:6751-6758 (1988).
Schwyzer, Ann. N.Y. Acad. Sci., 297:3-26 (1977).
Selby, et al., J. Neuroscience Res., 18:293-298 (1987).
Akiyama et al., J. Biol. Chem. (1985) 260(19):10402-10405.
Appel Ann. of Neurology (1981) 10(6):499-505.
Conolly et al., J. Cell Biol. (1981) 90:179-180.
Crutcher CRC Crit. Rev. in Clin. Neurol. (1986) 2(3):297-333.
Fabricant et al., Proc. Natl. Acad. Sci. (1977) 74(2):565:569.
Glinsky et al., Ann. New York Acad. Sci. (1987) 496:656-659.
Halegoua et al., Cell (1980) 22:571-581.
Hefti et al., Ann. of Neurol. (1986) 20(3):275-281.
Humphries et al., Science (1986) 233:467-470.
Korsching Tins (1986) Nov./Dec. pp. 570-573.

(List continued on next page.)

Prusiner New Eng. J. Med. (1987) 317:1571-1581.
Selkoe et al., Science (1987) 235:873-877.
Selkoe Tins (1987) 10(5):181-184.
St. George-Hyslop Science (1987) 235-885-890.
Tanzi et al., Science (1987) 235:880-884.
Williams clin. Res. (1988) Feb., pp. 5-10.

*Primary Examiner*—Merrell C. Cashion, Jr.
*Assistant Examiner*—Susan M. Perkins

[57] ABSTRACT

The present invention provides both agonist and antagonist nerve growth factor peptides. The NGF blocking peptides can be used to inhibit the expression of mRNA and their encoded proteins whose expression is stimulated by NGF, such as β-protein precursor and prion proteins, which proteins or their products are associated with neurodegenerative disorders, whereas the NGF agonist peptides can be used to treat neoplastic disorders such as neuroblastomas.

9 Claims, 7 Drawing Sheets

OTHER PUBLICATIONS

Mercanti et al., Bichim Biophys. Acta (1977) 496:412–419.
Mobley Soc. Neurosci. (1983) 9:270.
Prenner et al., Ann. of Allergy (1987) 58:332–335.
Romani et al., Int. J. Peptide Protein Res. (1987) 29:107–117.
Skaper et al., Brain Res. (1980) 197:379–389.
Tiercy et al., J. Cell Biol. (1986) 103:2367–2378.
Yu J. Biol. Chem. (1980) 255(21):10481–10492.
Anderton Nature (1987) 325:658–659.
Carrell Nature (1988) 331:478–479.
DeGrado et al., J. Organ. Chem. (1982) 45:1295–1300.
DeGrado et al., J. Organ. Chem. (1980) 45:1295–1300.
Deuel et al., Proq. Hematol. (1983) 13:201–221.
Greene et al., Ann. Rev. Neurosci. (1980) 3:352–402.
Johnson et al., Neurochem. Res. (1987) 12(11):985–994.
Levi-Montalcini Science (1987) 237:1154–1162.
Marx Science (1987) 238:1352–1353.
Meier et al., Embo J. (1986) 5(7):1489–1493.
Mobley et al., Mol. Brain Res. (1986) 1:53–62.
Mobley et al., Science (1985) 229:284–287.
Nakagawa et al., Science (1983) 48:678–685.
Plummer et al., Fed. Proc. (1983) 42:713 (Abstract No. 2466)

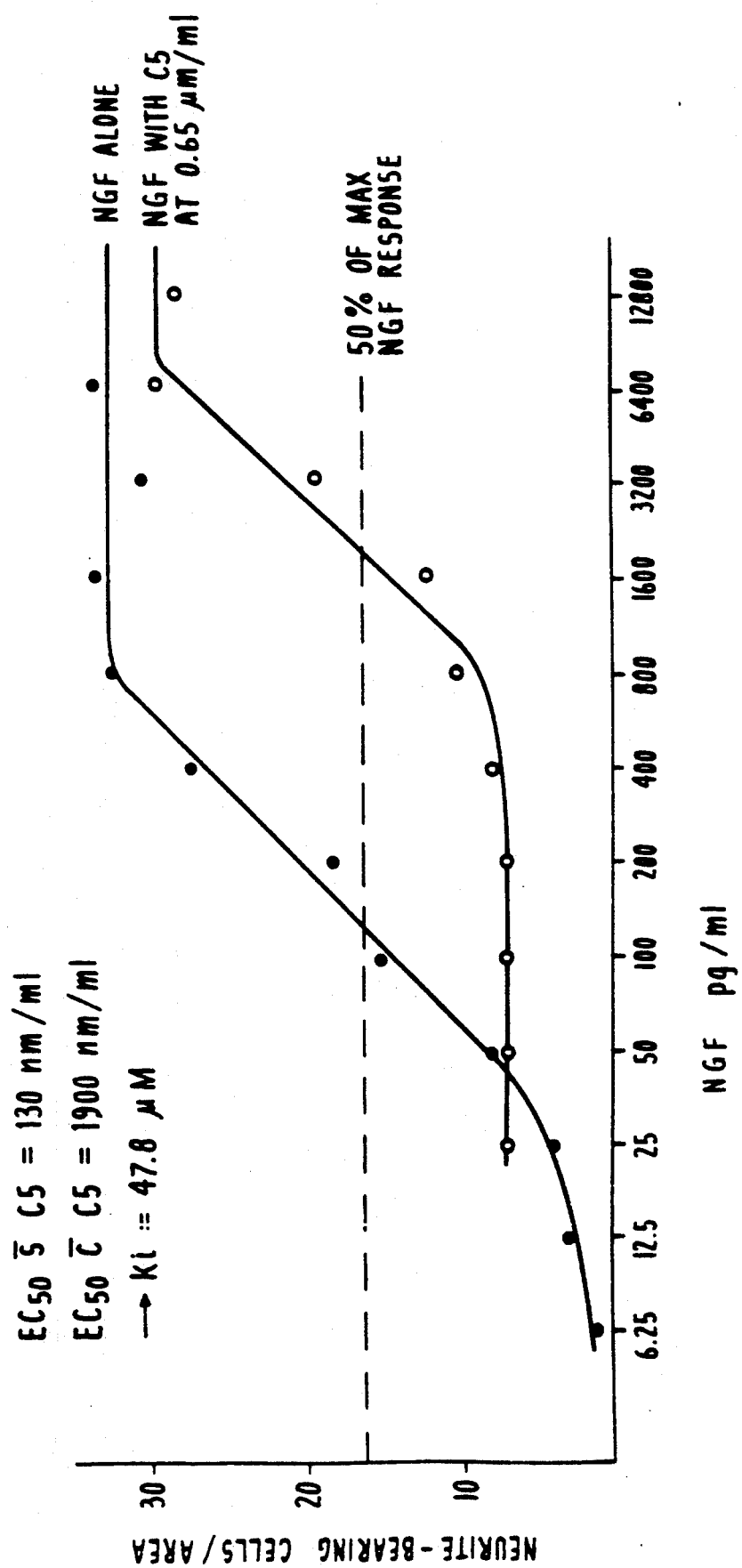

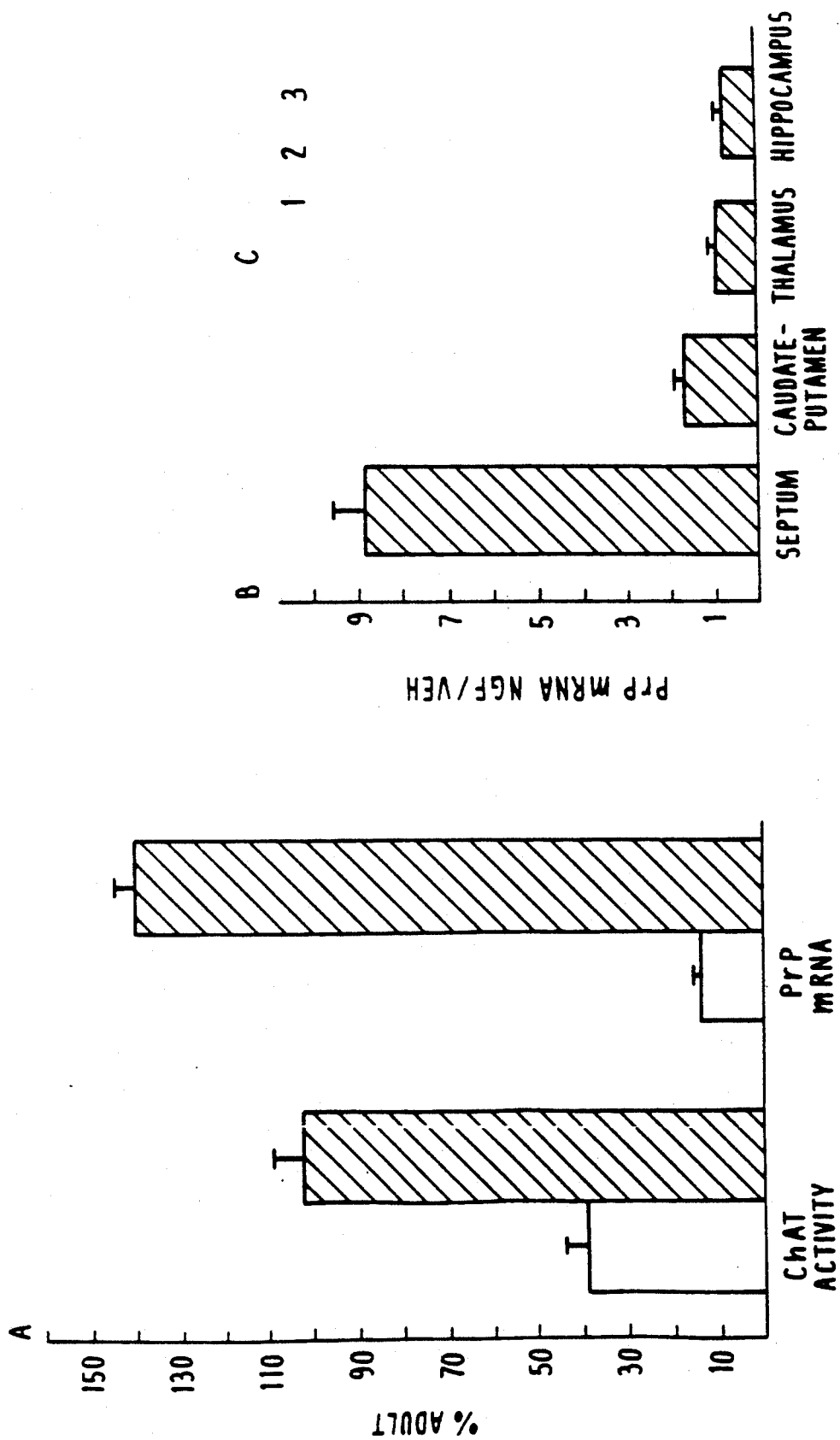

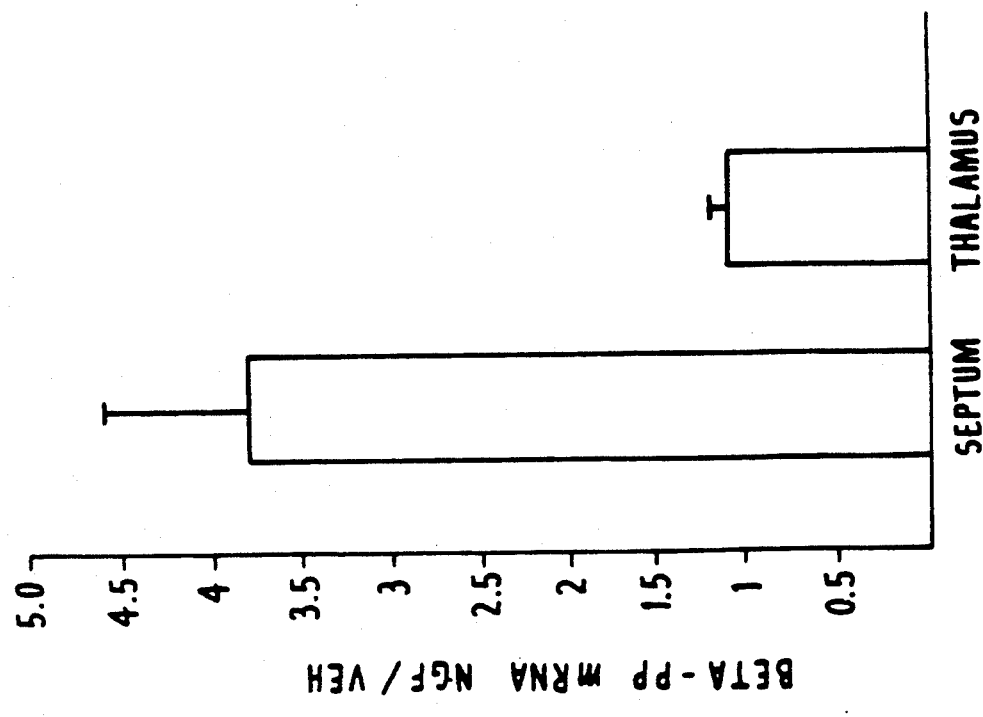

NERVE GROWTH FACTOR PEPTIDES

This invention was made with Government support under Grant No. NS 24054 awarded by the Department of Health and Human Services. The Government has certain rights in this invention.

Cross Reference to Related Application

This application is a continuation of application Ser. No. 299,698, filed Jan. 23, 1989, now abandoned, which is a continuation-in-part application of U.S. Ser. No. 173,975, filed Mar. 28, 1988, now abandoned.

TECHNICAL FIELD

This invention relates to neurotrophic factors and their involvement in neurodegenerative disorders. More particularly, this invention provides discrete peptides relating to nerve growth factor.

BACKGROUND

Nerve growth factor (NGF) is a protein which has prominent effects on developing sensory and sympathetic neurons of the peripheral nervous system. NGF acts via specific cell surface receptors on responsive neurons to support neuronal survival, promote neurite outgrowth, and enhance neurochemical differentiation. NGF actions are accompanied by alterations in neuronal membranes (Connolly et al, (1981) *J Cell Biol* 90:176-180; Skaper and Varon (1980) *Brain Res* 197:379-389), in the state of phosphorylation of neuronal proteins (Yu et al, (1980) *J Biol Chem* 255:10481-10492; Halegoua and Patrick (1980) *Cell* 22:571-581), and in the abundance of certain mRNA's and proteins likely to play a role in neuronal differentiation and function (see, for example, Tiercy and Shooter (1986) *J Cell Biol* 103:2367-2378).

Forebrain cholinergic neurons also respond to NGF and may require NGF for trophic support. Indeed, the distribution and ontogenesis of NGF and its receptor in the central nervous system (CNS) suggest that NGF acts as a target-derived neurotrophic factor for basal forebrain cholinergic neurons (Korschin, (1986) *TINS*, Nov/Dec, pp 570-573).

Deciphering the causation of human degenerative neurologic disorders has assumed increased importance with the realization that an increasing portion of the population may be affected. Trophic factors, such as NGF, are envisioned to have an important role in the development and maintenance of neurons (Crutcher (1986) *CRC Crit Rev Clin Neurobiol* 2:297-333), and it has been suggested that deficiencies in the supply or action of trophic factors may contribute to the loss of neurons in a number of neurodegenerative diseases (Appel (1981) *Ann Neurol* 10:499-505; Hefti and Weiner (1986) ibid 20:275-281).

As stated earlier, cholinergic neurons in the CNS also depend on NGF for survival. One major cholinergic pathway, from the basal forebrain to the hippocampus and neocortex (which responds to NGF), shows early, severe, relatively selective destruction in Alzheimer's disease. It is believed by some workers that NGF may aid in the survival and function of this neuronal population and thus provide a means for therapeutic treatment of Alzheimer's disease.

Amyloid plaques accumulate in the brain in various pathological states: Alzheimer's, Down's syndrome, normal aging, kuru, Creutzfeldt-Jacob disease, Gerstmann-Straussler syndrome, and other neurodegenerative disorders. The extent of amyloid accumulation in Alzheimer's brains correlates with the degree of mental impairment. It is possible that amyloid deposits cause such impairments. The mass of the accumulation itself can physically displace normal brain tissue (Mobley et al, (1983) *Soc Neurosci* 9:270). In addition, one of the amyloid proteins may promote neurite growth (Yanker et al (1988) *Soc Neurosci* 14:896; Schubert et al (1988) *Science* 241:223-226). In some of the above pathological states, massive tangles of neurites are associated with amyloid plaques. Inappropriate neurite growth could alter the maintenance and detour the formation of normal neurite-target connections.

While there has been a proposal that the accumulation of amyloid could be due to excessive amounts of NGF, up until the present invention, there has been no reported demonstration of NGF's involvement in the promotion of amyloid synthesis in animal brain.

It is also known that NGF is capable of encouraging tumor metastasis (Glinsky et al, (1987) *Annal New York Acad Sci* 496:656-659).

The general concept of using some portion of a protein to block the binding of the entire protein to its intended receptor is known. For example, the peptide Gly-Arg-Gly-Asp-Ser inhibits the colonization of a murine melanoma cell line in lungs of mice into which the melanoma cells were injected (Humphries et al, (1986) *Science* 255:467-470). This is apparently a result of inhibiting the ability of these cells to bind to the fibronectin, an extracellular matrix which contains this pentapeptide sequence (Akiyama et al, (1985) *J Biol Chem* 260:10402-10405). Also, the peptide His-Glu-Pro-Pro was able to compete with IgE (of which it is a subsequence) for binding to $F_cC$ receptors in human basophils; this tetrapeptide is thus considered a promising drug for the treatment of allergies (Prenner, (1987) *Annal of Allergy* 58:332-335).

A subunit of NGF has been proposed by Mercanti et al, (1977) *Biochem Biophys Acta* 494:412-419 to be an agonist of the full length molecule. However, Romani et al, (1987) *Int J Peptide Protein Res* 29:99-106; ibid. 107-117, after synthesizing this sequence (designated 10-27/75-88, according to the sequence correspondence in the disulfide linked dimer of identical 118 residue chains), analyzed the activity. The analysis showed that analog activity was not present in the synthetic fragment, nor was this subunit capable of inhibiting binding of NGF, although tested at very high concentration relative to the NGF itself.

Thus, while some peptides of NGF have been synthesized, to date, no one has identified biologically active peptides that retain one or more of the biological activities associated with NGF, nor have any NGF antagonists been identified.

DISCLOSURE OF THE INVENTION

The present invention provides a peptide having the ability to induce an NGF-associated biological response, wherein greater than 50% of the amino acid sequence of the peptide is at least 20% homologous with a receptor binding domain of NGF.

The present invention also provides NGF-related receptor-binding peptides having substantial homology to three discrete regions of native NGF. More particularly, one group of peptides comprises from 3 to 28 amino acid residues having substantial homology to residues 20-48 of native NGF (referred to at times herein as "Region C", with particular peptides within this region at times referred to as "C1", "C2", etc.), more preferably to residues 28-38 of NGF; a second group of peptides comprises from 3 to 34 amino acid residues having substantial homology to residues 50-84 of native NGF ("Region A"), more preferably to residues 66-75 of NGF; and a third group of peptides comprises from 3 to 25 amino acid residues having substantial homology to residues 87-112 of native NGF ("Region B"), more preferably to residues 98-106 of NGF.

Table 1, located herein in the *Modes for Carrying Out the Invention* section of this application, sets out the human and murine native sequences of the A, B, and C regions and lists the native sequences of the A1-A4, B1-B4 and C1-C13 subregions.

The peptides of this invention include the native regions and subregions as well as analogs of these sequences. These analogs include peptides which vary from the native material in any of the following ways:

1. Chemical modification of the amino and carboxyl groups present at the respective ends of the peptides.

2. Replacement of one or more of the amino acid residues in the native sequence with biologically compatible other amino acid resides.

3. Replacement of one or more of the amino acid residues in the native sequence with chemically modified biologically compatible other amino acid resides.

4. Deletion of one or more of the amino acid residues in the native sequence.

5. Repetition of one or preferably a sequence of several amino acid residues in the native sequence, with or without chemical modification to or replacement or deletion of one or more of the members of the sequence so as to give rise to "dimers", "trimers" and "polymers".

6. Cyclization, that is joining the ends, of a sequence of preferably a repeated sequence, such as a "dimer", etc.

The invention also provides as a preferred subgroup within the materials described above analogs of C2 NGF-related peptides exhibiting both agonist and antagonist properties in NGF bioassays. These analogs have the sequence:

$R_1\text{-}AA_1\text{-}AA_2\text{-}AA_3\text{-}AA_4\text{-}AA_5\text{-}AA_6\text{-}AA_7\text{-}AA_8\text{-}AA_9\text{-}R_2$ wherein:
AA$_1$ is a residue of an amino acid selected from the group Asp, D-Asp, Glu, D-Glu, Asn, D-Asn, Gln, D-Gln, and pyro-Glu, or can be deleted.
AA$_2$ is a residue of an amino acid selected from the group Ile, D-Ile, Val, D-Val, AdaA, AdaG, Leu, D-Leu, Met, and D-Met, or can be deleted;
AA$_3$ is a residue of an amino acid selected from the group Lys, D-Lys, Arg, D-Arg, Ile, D-Ile, Met, D-Met, homo-Arg, D-homo-Arg, Orn, and D-Orn, or can be deleted;
AA$_4$ is a residue of an amino acid selected from the group Gly, Ala, D-Ala, Pro, D-Pro, Aib, β-Ala, and Acp, or can be deleted;
AA$_5$ is- a residue of an amino, acid selected from the group Lys, D-Lys, Arg, homo-Arg, D-homo-Arg, Met, Ile, D-Arg, D-Met, D-Ile, Orn, and D-Orn, or can be deleted;
AA$_6$ is a residue of an amino acid selected from the group Glu, D-Glu, Gln, D-Gln, Asn, Asp, D-Asp, and D-Asn, or can be deleted;
AA$_7$ is a residue or an amino acid selected from the group Val, D-Val, Leu, D-Leu, Ile, D-Ile, Met, Chg, Cha, and D-Met, or can be deleted;
AA$_8$ is a residue of an amino acid selected from the group Thr, D-Thr, allo-Thr, Met, D-Met, Met(O) and d-Met(O), Ser, and D-Ser, or can be deleted;
AA$_9$ either is a residue of an amino acid selected from the group Val, D-Val, Leu, D-Leu, Chg, and Valinol, or together with R$_2$ forms

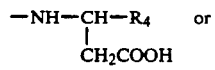   or

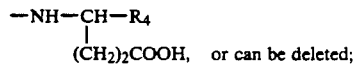

R$_1$ is attached to the amino group of AA$_1$ and selected from the group of hydrogen, lower alkyl, lower alkyl carbonyl, lower alkenyl, lower aklynyl, formyl, aryl, aroyl, aryloxy-carbonyl, aralkyloxy-carbonyl, lower alkyloxycarbonyl, benzoyl, 1- or 2-thenoyl, nicotinoyl, dihydronicotinoyl, N-alkyldihydronicotinoyl, isonicotinoyl, N-alkyldihydroisonicotinoyl, tetrahydronicotinoyl, and N-alkyltetrahydronicotinoyl;

R$_2$ is attached to the carbonyl group carbon of AA$_9$ and selected from the group of OH, NH$_2$, OR$_3$, OR$_3$OH, and NHR$_3$ with NH$_2$ and NHR$_3$ being preferred;

R$_3$ is selected from the group of lower alkyl and aryl groups; and

R$_4$ is selected from the group of PO$_3$H$_2$, B(OH)$_2$, CH$_2$OH, SO$_3$H, and

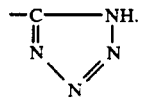

Preferably at least five, and even more preferably at least eight, of AA$_1$ through AA$_9$ are selected from the native NGF C2 sequence in which AA$_1$ is Asp, AA$_2$ is Ile, AA$_3$ is Lys, AA$_4$ is Gly, AA$_5$ is Lys, AA$_6$ is Glu, AA$_7$ is Val, AA$_8$ is Thr, and AA$_9$ is Val. Other preferred configurations in the C2 region employ the native sequence with R$_2$ as NH$_2$ or the native sequence with the AA$_8$ Thr deleted and R$_2$ as NH$_2$.

Yet other materials of the invention are analogs of the C5 NGF-related peptide. These display strong NGF antagonist properties and have the sequence:

$R_1\text{-}AA_2\text{-}AA_3\text{-}AA_4\text{-}R_2$ wherein:
AA$_1$ is a residue of an amino acid selected from the group Lys, D-Lys, Arg, D-Arg, Pro, D-Pro, Nle, homo-Arg, D-homo-Arg, Orn and D-Orn or can be deleted.
AA$_2$ is a residue of an amino acid selected from the group consisting of: Val, d-Val, Gly, Pro, D-PrO, Ala, D-Ala, Aib, Leu, D-Leu, Ile, and D-Ile or can be deleted;
AA$_3$ is a residue of an amino acid selected from the group Lys, D-Lys, Arg, D-Arg, Pro, D-Pro, and Nle or can be deleted;
AA$_4$ either is a residue of an amino acid selected from the group consisting of: Glu, D-Glu, Gln, D-Gln, Asp, D-Asp, Asn, D-Asn, Phe, and D-Phe, or can be deleted, or together with $R_2$ forms

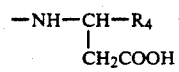

or

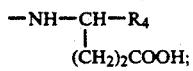

$R_1$ is attached to the amino group of $AA_1$ and selected from the group of hydrogen, lower alkyl, lower alkyl carbonyl, lower alkenyl, lower alkynyl, formyl, aryl, aroyl, aryloxy-carbonyl, aralkyloxy-carbonyl, lower alkyloxycarbonyl, benzoyl, 1- or 2-thenoyl, nicotinoyl, dihydronicotinoyl, N-alkyl-dihydronicotinoyl, isonicotinoyl, N-alkyldihydroisonicotinoyl, tetrahydronicotinoyl, and N-alkyltetrahydronicotinoyl;

$R_2$ is attached to the carbonyl group carbon of $AA_4$ and selected from the group of OH, $NH_2$, $OR_3$, $OR_3OH$, and $NHR_3$ with $NH_2$ and $NHR_3$ being preferred;

$R_3$ is selected from the group of lower alkyl and aryl groups; and $R_4$ is selected from the group of $PO_3H_2$, $B(OH)_2$, $CH_2OH$, $SO_3H$, and

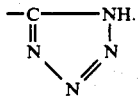

Preferably at least two, and more preferably three, of $AA_1$, $AA_2$, $AA_3$ and $AA_4$ are selected from the native C5 NGF sequence in which $AA_1$ is Lys, $AA_2$ is Gly, $AA_3$ is Lys and $AA_4$ is Glu, preferably with $R_2$ as $NH_2$ or $NHR_3$. Also it is preferred that the C5 materials contain at least 3 and at most 5 amino acid residues.

When any peptide of the invention includes a glutamic or aspartic acid residue, its free OH group can be replaced by any of the groups listed above for $R_2$.

The invention also provides a method of inhibiting NGF-mediated biochemical or biophysical cellular effects which comprises applying an NGF antagonist peptide to NGF responsive cells.

Another aspect of the invention is a method of inhibiting the expression of mRNA or their encoded proteins by cells, the expression of which is stimulated by NGF, wherein the method comprises applying an NGF antagonist peptide of the invention to the cells.

Yet another aspect of the invention is a method for treatment of disorders involving NGF-responsive cells, which method comprises administering an effective amount of one or more of the present peptides to an individual suffering from such a disorder.

Pharmaceutical compositions composed of the peptides are also disclosed herein.

BRIEF DESCRIPTION OF THE DRAWINGS

FIGS. 1A and 1B are graphs which depict the results of NGF antagonist inhibition assays using increasing concentrations of the C1, C2, and C5 peptide and a fixed concentration of NGF (1A), or increasing concentrations of NGF with a fixed concentration of C5 (1B).

The NGF bioeffect being referred to is the promotion of neurite outgrowth.

Figure 2:
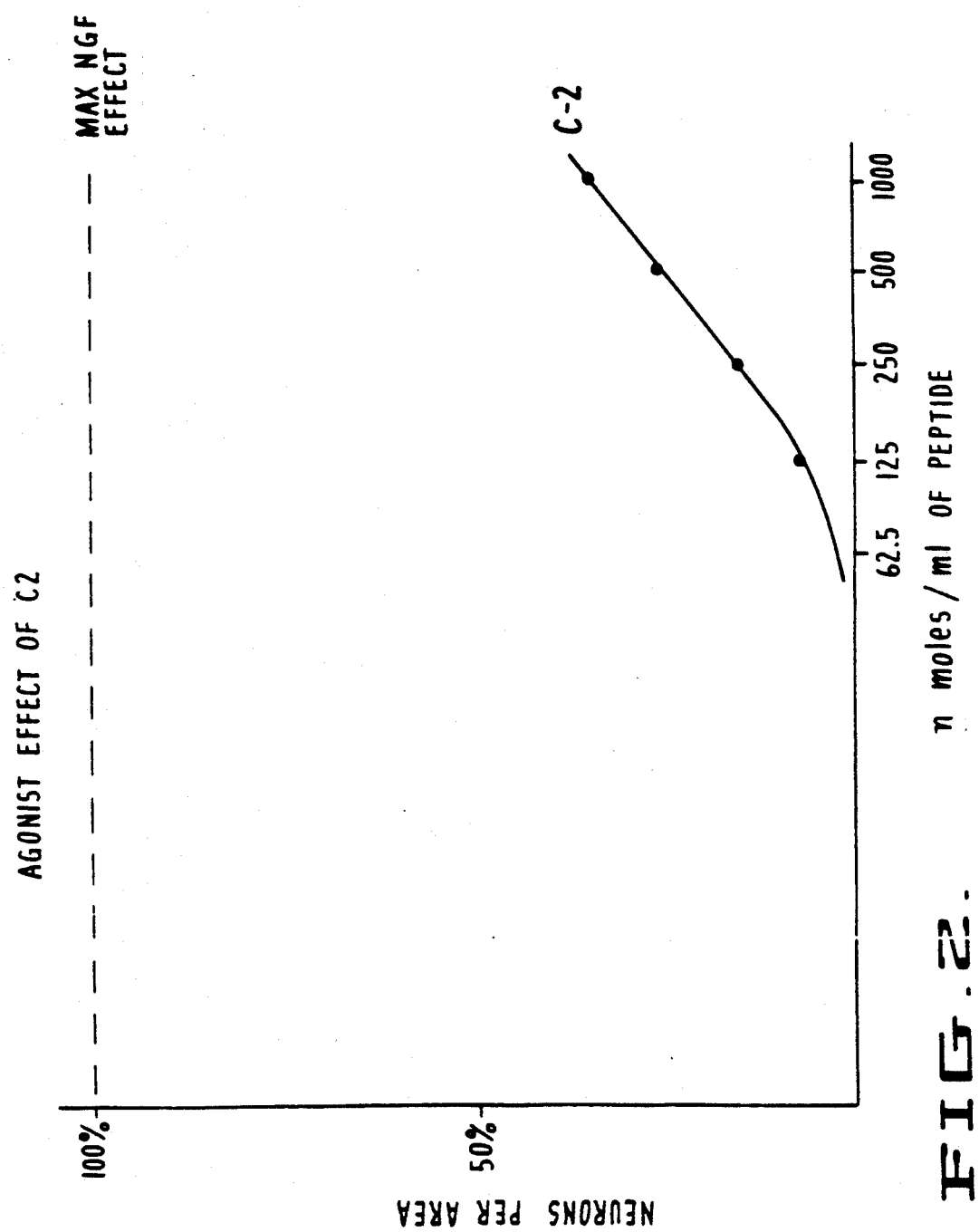

FIG. 2 demonstrates agonist activity of C2 peptide.

Figure 3:
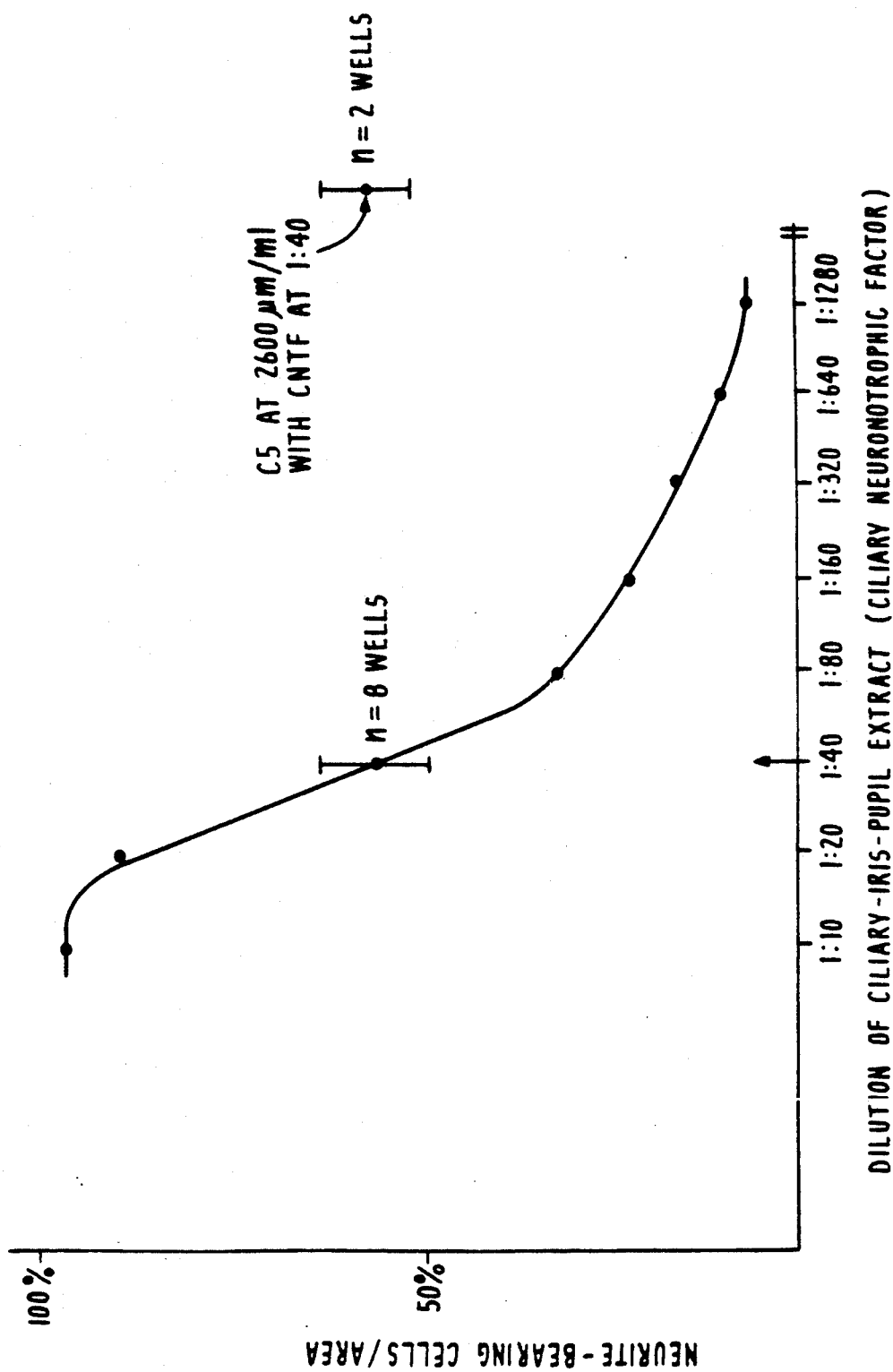

FIG. 3 is a dose/response curve for the effect of CNTF on day 10 dorsal root ganglion neurons. C5 had no effect on CNTF activity.

Figure 4:
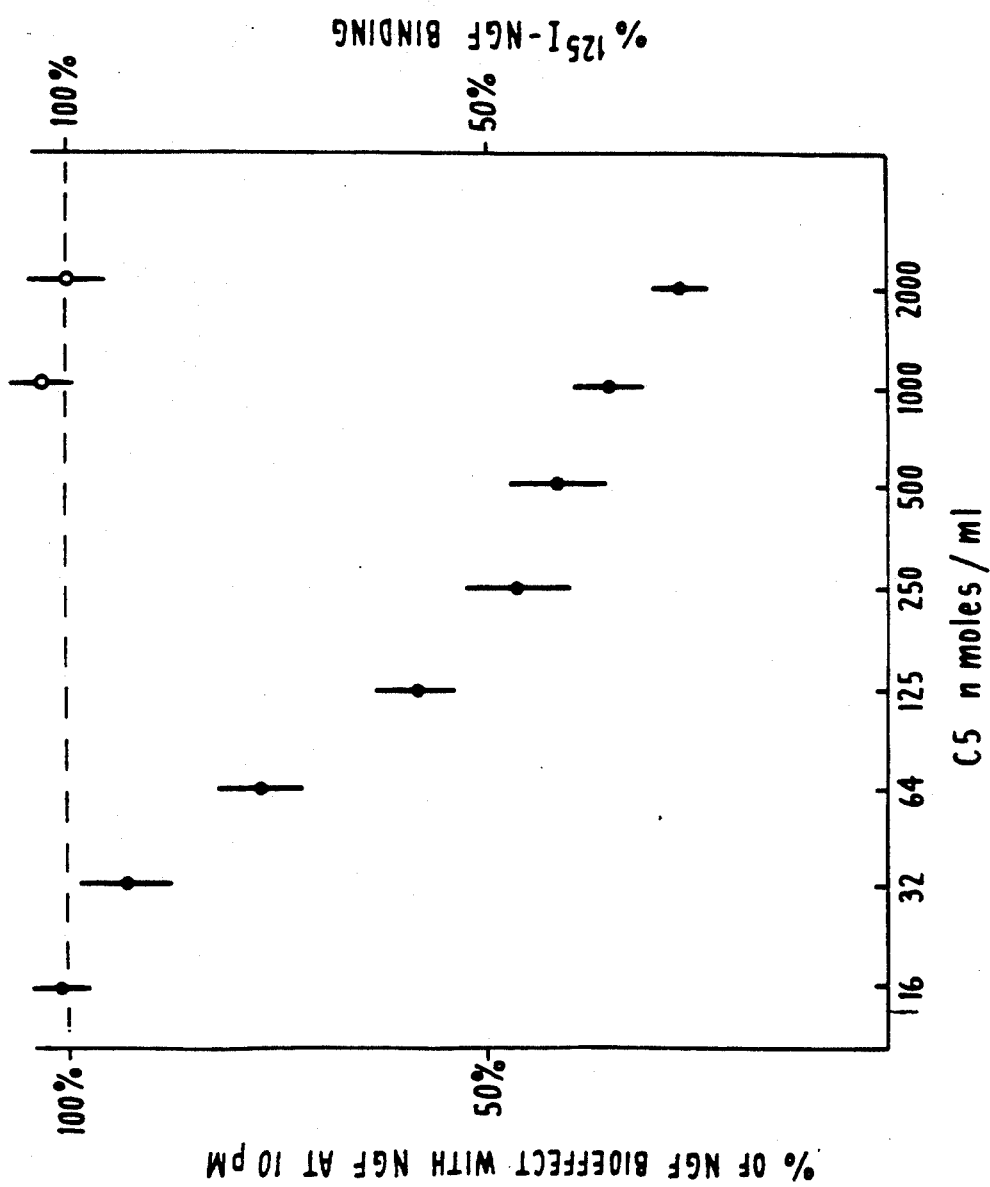

FIG. 4 is a comparison of the concentration ranges through which C5 inhibits the NGF bioeffect (i.e. neurite outgrowth) without altering NGF binding.

FIGS. 5A and 5B illustrate the response of ChAT activity and of PrP mRNA levels to NGF treatment.

FIG. 6 demonstrates the response of β-protein precursor mRNA to NGF treatment.

MODES FOR CARRYING OUT THE INVENTION

A. Definitions

For purposes of the present invention the following terms are defined below.

"Agonist" refers to an NGF peptide capable of promoting at least one of the biological responses normally associated with NGF. For example, an NGF agonist may promote neurite growth but fail to enhance neurochemical differentiation in NGF responsive neurons.

"Antagonist" refers to an NGF peptide that opposes at least one of the effects of NGF. In the presence of an antagonist, NGF has reduced ability to mediate biological responses normally associated with NGF.

An NGF receptor binding domain is any region of the NGF molecule which interacts directly or indirectly with the NGF receptor. Such interaction is intended to include any covalent or non-covalent interactions. The putative receptor binding domains for NGF, as numbered to correspond to the murine β-NGF sequence, include amino acid residues 20–48 (Region C), 50–84 (Region A) and 87–112 (Region B).

"Substantial homology" as used herein refers to substantial correspondence between the identity and sequence of amino acid residues of the native, murine NGF protein and the synthetic peptides. More particularly, at least half of the residues in the synthetic peptides correspond to the residues present in the native molecule.

Murine NGF may be readily isolated from the submaxillary gland of male mice. This murine NGF is expressed as a 7S complex, containing the NGF-α, β and δ subunits. Alternatively, the NGF may be produced by recombinant DNA techniques as disclosed in European Patent Publication 121,338, published Oct. 10, 1984, the disclosure of which is incorporated herein by reference. β-NGF is a dimer of two identical 118 amino acid chains, and is apparently solely responsible for the observed biological activity of NGF. As used herein, "NGF" refers to β-NGF.

The primary sequence for NGF molecules from five different species have been determined (Meier et al, (1986) *EMBO J* 5(7):1489–1493). Studies on the biological relatedness of NGF's purified from different species strongly support the hypothesis that the site (or sites) of interaction with their receptors has remained structurally constant. For purposes of the present invention, the NGF sequence can be derived from any mammalian source, including, for example, murine or human origin, since the homology between the receptor binding domains among mammalian species is extremely high. Table 1 shows the comparison for Regions A, B and C between murine and human NGF.

The term "effective amount" refers to the amount of NGF peptide needed to produce a desired manifestation or blocking of NGF activity. The precise amount will vary with the particular NGF peptide employed, the age and condition of the subject to be treated, and the nature and severity of the condition. However, the effective amount may be determined by one of ordinary skill in the art with only routine experimentation, following the methodology described herein.

As used herein, the terms "NGF-mediated activity" or "NGF-associated activity" refers to cellular events triggered by NGF. The nature of these activities may be biochemical or biophysical. The following list is provided, without limitation, which discloses some of the known activities associated with NGF: ion flux, phospholipid metabolism, activation of cyclic AMP-dependent protein kinase, activation of cyclic AMP-independent protein kinase and other protein kinases, protein phosphorylation, activation of oncogenic proteins, activation of RNA transcription, stabilization of mRNA species, and enhancement of protein synthesis.

The terms "disorder" or "neurodegenerative disorder" as used herein refer to a disease state in a mammal which can include degenerative growth and development disorders, chromosomal abnormalities, viral infections and disorders of the nervous system or neoplastic conditions which can respond to treatment with the NGF-derived peptides. Thus, diseases characterized by the loss of function and/or degeneration of neurons and nerves are within the scope of the invention. In addition, any disease that can respond to treatment of NGF-responsive or NGF-synthesizing cells with the present peptides is within the scope of the invention. Exemplary cell types include without limitation, cholinergic neurons, sensory and sympathetic neurons, adrenal medullary cells, Schwann cells, fibroblasts, smooth muscle cells, astroglial cells, macrophages, epithelial cells, and melanoma cells. Exemplary disorders include without limitation, Alzheimer's disease, Down's syndrome, Creutzfeldt-Jacob disease, kuru, Gerstman-Straussler syndrome, scrapie, transmissible mink encephalopathy, Huntington's disease, Riley-Day familial dysautonomia, multiple system atrophy, and the like. Also considered within this definition is the treatment of injury to the nervous system. Additionally, neural tumors, such as neuroblastoma, involving either neurons or their supporting elements, may be responsive to treatment with NGF and NGF agonists. NGF antagonists would find utility in treating pathological events which may be enhanced by NGF, such as the treatment of tumors or tumor metastasis (Ginsky, supra).

The amino terminal substituent ($R_1$) of the NGF peptides includes: hydrogen, lower alkyls having from 1 to 4 carbons such as methyl, ethyl, propyl and butyl and their amide-yielding lower alkyl carbonyl forms such as formyl and acetyl; lower alkenyls, such as ethenyl, and prop-1-enyl and prop-2-enyl; lower alkynyls such as ethynyl and the propynyls; an aryl group such as phenyl or naphthyl; an aroyl group such as benzoyl or naphthoyl; an aryloxy-carbonyl such as

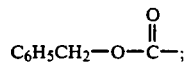

an aralkyloxy-carbonyl such as

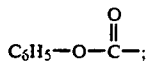

and a lower alkyloxycarbonyl such as

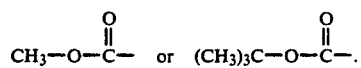

Hydrogen is a preferred $R_1$ substituent.

The carboxy terminal substituent ($R_2$) of the NGF peptides includes: OH; $NH_2$; and $OR_3$, such that the carboxy terminus is a lower alkyl or aryl ester, wherein $R_3$ is a lower alkyl having from 1 to 4 carbons or an aryl group of 6 to 10 carbons; $OR_3OH$ such that the terminus is a hydroxy-substituted ester with R3 defined as above; NH-$R_3$, wherein $R_3$ is defined as above, and $PO_3H_2$, $B(OH)_2$, $CH_2OH$, $SO_3H$ and 5-tetrazole which replaces the COOH of the carboxyl-terminal amino acid.

B. NGF Peptides

The nomenclature used to define the peptides is that specified by Schroder & Lubke, "The Peptides", Academic Press (1965), wherein in accordance with conventional representation, the amino group at the N-terminus appears to the left and the carboxyl group at the C-terminus to the right. By natural amino acid is meant one of common, naturally occurring amino acids found in proteins comprising Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y) and Val (V). By Nle is meant norleucine, by Aib is meant aminoisobutyric acid, by AdaA is meant α-adamantylalanine, by AdaG is meant β-adamantylglycine, by homo-Arg is meant 1-homoarginine, by D-homo-Arg is meant D-homoarginine, by Acp is meant epsilon-amino caproic acid, by Chg is meant 1-α-cyclohexylglycine, and by allo-Thr is meant 1-allothreonine. Additionally, by Cha is meant β-cyclohexyl-alanine, by Me is meant methyl ($CH_3$), by Orn is meant ornithine, by, pyro-Glu is meant the pyroglutamyl group, by Met(O) and D-Met(O) are meant the sulfoxides derived from l- and D-methionine, respectively, and by β-Ala is meant β-alanine.

The symbolism and abbreviations used are otherwise those recommended by the "IUPAC-IUB Joint Commission on Biochemical Nomenclature, Nomenclature and Symbolism for Amino Acids and Peptides, Recommendations 1983." As is conventional, these same symbols will be used to define the corresponding residues of the acids when they are linked into a peptide chain. Where the amino acid residue has isomeric forms, it is the L-form of the amino acid that is represented unless otherwise expressly indicated.

Studies on the effects of exogenous NGF have provided important clues regarding the role of NGF in the normal growth and development of target neurons. The data which most clearly indicates a physiological role for endogenous NGF comes from studies of the effect of NGF antibodies on the growth and development of responsive neuronal populations. A significant limitation in the performance of antibody experiments, and their interpretation, lies in the degree to which antibodies have access to NGF. This limitation is especially noteworthy for studies of NGF actions in the central nervous system.

Another method for studying the role of trophic factors such as NGF, involves inhibiting the action of polypeptides by blocking binding of the polypeptide to its specific receptor. The primary requirement is to identify regions of the polypeptide likely to interact with these receptors. Though there is a great deal of data regarding structural and functional characteristics of the interaction of NGF with its receptor (see Yankner and Shooter (1982) *Ann Rev Biochem* 51:845–868), the regions of NGF involved in receptor binding are as yet unknown. If one predicts that NGF interacts with its receptor via hydrophilic domains, and that these domains are highly conserved through evolution, one can make informed guesses as to which regions may mediate binding. However, there are no clear criteria for quantitatively predicting the degree of agonist or antagonist activity of a given peptide.

From the known amino acid sequence of NGF, three regions were investigated as possible receptor binding domains. Region A (residues 50–84), Region B (residues 87–112) and Region C (residues 20–48) were chosen because of their relatively high degree of hydrophilicity, cross-species conservation, or the probability of containing a β-turn. The specific peptides listed in Table 1 below, each synthesized with their carboxy terminus in the amide form, were tested for their ability to block NGF activity or, in the case of agonists, to support neuronal survival as described in the examples which follow. The sequences provided for each of the three regions are provided; the human sequence is illustrated beneath the murine sequence.

TABLE 1

Native Amino Acid Sequences For A, B and C Regions and Subregions

| Region A: | | Region B: | | Region C: | |
|---|---|---|---|---|---|
| Murine: | | Murine: | | Murine: | |
| SGCRGIDSKH | | AWRFIRIDT | | ATDIKGKEVTV | |
| Human: | | Human: | | Human: | |
| SGCRGIDSKH | | AWRFIRIDT | | ATDIKGKEVMV | |
| A1 | SGCRGIDSKH | B1 | AWRFIRIDT | C1 | ATDIKGKEVTV |
| A2 | RGIDSKH | B2 | RIDT | C2 | DIKGKEVTV |
| A3 | RGIDS | B3 | RFIRIDT | C3 | KGKEVTV |
| A4 | RDISDK | B4 | RFIRID | C4 | DIKGKE |
| | | | | C5 | KGKE |
| | | | | C6 | DIKG |
| | | | | C7 | KGK |
| | | | | C8 | IKG |
| | | | | C9 | IKGK |
| | | | | C10 | ATDIKG |
| | | | | C11 | GKEV |
| | | | | C12 | GKE |
| | | | | C13 | KG |

Other representative analogs falling within the scope of this invention include the following C5 and C2 analogs:

C5 ANALOGS
Glu-4 Modifications

Lys—Gly—Lys-Glutamic Acid

Lys—Gly—Lys—NH—CH—CH$_2$OH
$\quad\quad\quad\quad\quad\quad\quad\quad$|
$\quad\quad\quad\quad\quad\quad\quad\quad$CH$_2$CH$_2$COOH Lys—Gly—Lys—Glu—NH—CH$_3$ Lys—Gly—Lys—Gln—OH Lys—Gly—Lys—Gln—NH$_2$ Lys—Gly—Lys-D-Glu—NH$_2$ Lys—Gly—Lys—NH—CH—PO$_3$H$_2$
$\quad\quad\quad\quad\quad\quad\quad\quad$|
$\quad\quad\quad\quad\quad\quad\quad\quad$CH$_2$CH$_2$COOH Lys—Gly—Lys—Gln—NH$_2$ Lys—Gly—Lys—NH—CH—CH$_2$OH
$\quad\quad\quad\quad\quad\quad\quad\quad$|
$\quad\quad\quad\quad\quad\quad\quad\quad$CH$_2$CH$_2$COOH Lys—Gly—Lys—NH—CH—CH$_2$OH
$\quad\quad\quad\quad\quad\quad\quad\quad$|
$\quad\quad\quad\quad\quad\quad\quad\quad$CH$_2$CH$_2$—CH$_2$OH Lys—Gly—Lys—NH—CH—CONH$_2$
$\quad\quad\quad\quad\quad\quad\quad\quad$|
$\quad\quad\quad\quad\quad\quad\quad\quad$CH$_2$CH$_2$—CH$_2$OH Lys—Gly—Lys—Glu—NH$_2$ Lys—Gly—Lys—Phe—NH$_2$

Lys-3 Modifications

Lys—Gly—Arg—Glu—NH$_2$

Lys—Gly—Arg—Glu—NH—CH$_3$

Lys—Gly—Arg—Gln—OH

Lys—Gly—Nle—Glu—NH$_2$

Lys—Gly—Pro—Glu—NH$_2$

Lys—Gly—Pro—NH—CH—PO$_3$H$_2$
$\quad\quad\quad\quad\quad\quad\quad\quad$|
$\quad\quad\quad\quad\quad\quad\quad\quad$CH$_2$CH$_2$COOH

Gly-2 Modifications

Lys—Pro—Lys—Asp—NH—CH$_3$

Lys—Ala—Lys—Glu—NH—CH$_3$

Lys—Val—Lys—Glu—NH$_2$

Lys—Pro—Lys—Glu—NH—CH$_3$

Lys-D-Ala—Lys—Glu—NH$_2$

Lys—Ala—Lys—Glu—NH$_2$

-continued

Lys-D-Ala—Lys—Glu—NH$_2$

Lys—Aib—Lys—Glu—NH$_2$

Lys—Leu—Lys—Glu—NH$_2$

Lys-1 Modifications

Orn—Gly—Lys—Glu—NH$_2$

D-Orn—Gly—Lys—Glu—NH$_2$

D-Lys—Gly—Lys—Glu—NH$_2$

D-Lys-D-Ala—Lys—Glu—NH$_2$

D-Lys—Gly—Lys—Glu—NH—CH$_3$

Arg—Gly—Lys—Glu—NH$_2$

D-Arg—Gly—Lys—Glu—NH$_2$

Arg—Gly—Lys—Glu—NH—CH$_3$

Arg—Gly—Arg—Glu—NH$_2$

D-Lys—Gly—Arg—Asp—NH$_2$ homo-Arg—Gly—Lys—Glu—NH$_2$

D-homo-Arg—Gly—Lys—Glu—NH$_2$

Dimers

Lys—Gly—Lys—Glu—Lys—Gly—Lys—Glu—NH$_2$

Lys—Gly—Lys—Glu-β-Ala—Lys—Gly—Lys—Glu—NH$_2$

Lys—Gly—Lys—Gln-β-Ala—Lys—Gly—Lys—Gln—NH$_2$

Polymeric Peptides Wherein n is an Integer Between 2 and 40

(Lys—Gly—Lys—Glu)$_n$—R$_2$
            |
            NH$_2$ (Lys—Gly—Lys—Glu)$_n$—R$_2$ (Lys—Gly—Lys—Glu—Gly)$_n$—R$_2$ (Lys—Gly—Lys—Glu-β-Ala)$_n$—R$_2$ (Lys—Gly—Lys—Glu—Pro)$_n$—R$_2$

Cyclic Analogs

Cyclo(-Lys—Gly—Lys—Glu—Lys—Gly—Lys—Glu—)

Cyclo(-Lys—Gly—Lys—Glu—Pro—

—Lys—Gly—Lys—Glu—Pro—)

Cyclo(-Lys—Gly—Lys—Glu-β-Ala—

—Lys—Gly—Lys—Glu-β-Ala—)

Selective acylation of side chain NH$_2$ group of Lys-1 or 3

Lys—Gly—Lys—Glu—NH$_2$
 |
 Ac

Lys—Gly—Lys—Glu—NH$_2$
         |
         Ac

Lys—Gly—Lys—Glu—NH$_2$
 |
 Bz

-continued

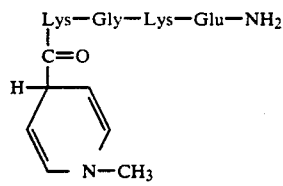

Lys—Gly—Lys—Glu—Acp-analogs:

Lys—Gly—Lys—Glu—Acp—OH

Lys—Gly—Lys—Glu—Acp—NH$_2$

Lys—Gly—Lys—Glu—NH(CH$_2$)$_6$—OH

Lys—Ala—Lys—Glu—Acp—OH

Lys—Pro—Lys—Glu—Acp—OH

Lys—Ala—Lys—Glu—Acp—NH$_2$

Lys—Pro—Lys—Glu—Acp—NH$_2$

Lys—Ala—Lys—Glu—Acp—CH$_2$OH

Lys—Pro—Lys—Glu—NH(CH$_2$)$_6$—OH

C2 ANALOGS

Asp-1 Modifications

D-Asp—Ile—Lys—Gly—Lys—Glu—Val—Thr—Val—R$_2$*

D-Asp—Ile—Lys—Gly—Lys—Glu—Val—Thr—Val—OH

D-Asp—Ile—Lys—Gly—Lys—Glu—Val—Thr—Val—OCH$_3$

D-Asp—Ile—Lys—Gly—Lys—Glu—Val—Thr—Val—NH$_2$

D-Asp—Ile—Lys—Gly—Lys—Glu—

—Val—Thr—Val—NH—CH$_3$

D-Asp—Ile—Lys—Gly—Lys—Glu—Val—Thr—Val—PO$_3$H$_2$

Glu—Ile—Lys—Gly—Lys—Glu—Val—Thr—Val—R$_2$

Asn—Ile—Lys—Gly—Lys—Glu—Val—Thr—Val—R$_2$

Gln—Ile—Lys—Gly—Lys—Glu—Val—Thr—Val—R$_2$

D-Glu—Ile—Lys—Gly—Lys—Glu—Val—Thr—Val—R$_2$

D-Gln—Ile—Lys—Gly—Lys—Glu—Val—Thr—Val—R$_2$

Ile-2 Modifications

Asp—Leu—Lys—Gly—Lys—Glu—Val—Thr—Val—R$_2$

Asp—Val—Lys—Gly—Lys—Glu—Val—Thr—Val—R$_2$

Asp—AdaA—Lys—Gly—Lys—Glu—Val—Thr—Val—R$_2$

Asp—AdaG—Lys—Gly—Lys—Glu—Val—Thr—Val—R$_2$

Asp—D-Ile—Lys—Gly—Lys—Glu—Val—Thr—Val—R$_2$

Asp—D-Leu—Lys—Gly—Lys—Glu—Val—Thr—Val—R$_2$

Asp—D-Val—Lys—Gly—Lys—Glu—Val—Thr—Val—R$_2$

Asp—Cha—Lys—Gly—Lys—Glu—Val—Thr—Val—R$_2$

Lys-3 Modifications

Asp—Ile-D-Lys—Gly—Lys—Glu—Val—Thr—Val—R$_2$

Asp—Ile—Arg—Gly—Lys—Glu—Val—Thr—Val—R$_2$

-continued

Asp—Ile-homo-Arg—Gly—Lys—Glu—Val—Thr—Val—R$_2$

Asp—Ile-D-Arg—Gly—Lys—Glu—Val—Thr—Val—R$_2$

Asp—Ile—Ile—Gly—Lys—Glu—Val—Thr—Val—R$_2$

Asp—Ile—Met—Gly—Lys—Glu—Val—Thr—Val—R$_2$

Asp—Ile-D-Orn—Gly—Lys—Glu—Val—Thr—Val—R$_2$

D-Gln—Leu-D-Lys—Gly—Lys—Glu—Val—Thr—Val—R$_2$

D-Asp—Leu-D-Lys—Gly—Lys—Glu—Val—Thr—Val—R$_2$

Gly-4 Modifications

Asp—Ile—Lys—Ala—Lys—Glu—Val—Thr—Val—R$_2$

Asp—Ile—Lys—Aib—Lys—Glu—Val—Thr—Val—R$_2$

Asp—Ile—Lys—Ala—Lys—Glu—Val—Thr—Val—R$_2$

Asp—Ile—Lys-β-Ala—Lys—Glu—Val—Thr—Val—R$_2$

Asp—Ile—Lys—Acp—Lys—Glu—Val—Thr—Val—R$_2$

D-Asp—Ile—Lys-D-Ala—Lys—Glu—Val—Thr—Val—R$_2$

Asp—Ile—Lys-D-Pro—Lys—Glu—Val—Thr—Val—R$_2$

Lys-5 Modifications

Asp—Ile—Lys—Gly-D-Lys—Glu—Val—Thr—Val—R$_2$

Asp—Ile—Lys—Gly—Arg—Glu—Val—Thr—Val—R$_2$

Asp—Ile—Lys—Gly—Arg—Glu—Val—Thr—Val—R$_2$

Asp—Ile—Lys—Gly-homo-Arg—Glu—Val—Thr—Val—R$_2$

Asp—Ile—Lys—Gly—Met—Glu—Val—Thr—Val—R$_2$

Asp—Ile—Lys—Gly—Ile—Glu—Val—Thr—Val—R$_2$

Asp—Ile—Lys—Pro-D-Arg—Glu—Val—Thr—Val—R$_2$

Asp—Ile—Lys—Pro-D-Orn—Glu—Val—Thr—Val—R$_2$

Glu-6 Modifications

Asp—Ile—Lys—Gly—Lys-D-Glu—Val—Thr—Val—R$_2$

Asp—Ile—Lys—Gly—Lys—Asp—Val—Thr—Val—R$_2$

Asp—Ile—Lys—Gly—Lys-D-Asp—Val—Thr—Val—R$_2$

Asp—Ile—Lys—Gly—Lys—Gln—Val—Thr—Val—R$_2$

Asp—Ile—Lys—Gly—Lys—Asn—Val—Thr—Val—R$_2$

Asp—Ile—Lys—Pro—Lys-D-Glu—Val—Thr—Val—R$_2$

Val-7 Modifications

Asp—Ile—Lys—Gly—Lys—Glu—Leu—Thr—Val—R$_2$

Asp—Ile—Lys—Gly—Lys—Glu—Ile—Thr—Val—R$_2$

Asp—Ile—Lys—Gly—Lys—Glu—Met—Thr—Val—R$_2$

Asp—Ile—Lys—Gly—Lys—Glu—Val—Thr—Val—R$_2$

Asp—Ile—Lys—Gly—Lys—Glu—Chg—Thr—Val—R$_2$

Asp—Ile—Lys-D-Pro—Lys—Glu—Leu—Thr—Val—R$_2$

Thr-8 Modifications

Asp—Ile—Lys—Gly—Lys—Glu—Val—Ser—Val—R$_2$

-continued

Asp—Ile—Lys—Gly—Lys—Glu—Val-D-Thr—Val—R$_2$

Asp—Ile—Lys—Gly—Lys—Glu—Val-allo-Thr—Val—R$_2$

Asp—Ile—Lys-1-Pro—Lys—Glu—Val—Ser—Val—R$_2$

Asp—Ile—Lys-1-Pro—Lys—Glu—Val—Leu—Val—R$_2$

Asp—Ile—Lys—Gly—Lys—Glu—Val—Met—Val—R$_2$

Asp—Ile—Lys—Gly—Lys—Glu—Val—Val—R$_2$

Val-9 Modifications

Asp—Ile—Lys—Gly—Lys—Glu—Val—Met—Leu—R$_2$

Asp—Ile—Lys—Gly—Lys—Glu—Val—Met—Met—R$_2$

Asp—Ile—Lys—Gly—Lys—Glu—Val—Met—Chg—R$_2$

Asp—Ile—Lys—Gly—Lys—Glu—Val—Met-Valinol

Dimers (Asn—Ile—Lys—Gly—Lys—Gln—Val—Thr—Val)$_2$NH$_2$ (Asp—Ile—Lys—Gly—Lys—Glu—Val—Thr—Val)$_2$—OH (Asp—Ile—Lys—Gly—Lys—Glu—Val—Thr—Val)$_2$(Gly)—R$_2$ (Asp—Ile—Lys—Gly—Lys—Glu—Val—Thr—Val)$_2$(Pro)—R$_2$ (Asp—Ile—Lys—Gly—Lys—Glu—Val—Thr—Val)$_2$β-Ala—R$_2$ Cyclic Analogs Cyclo(-Asp—Ile—Lys—Gly—Lys—Glu—Val—Thr—Val—)

Cyclo(-Asp—Ile—Lys—Gly—Lys—Gln—Val—Thr—Val—)

Cyclo(-Asp—Ile—Lys—Gly—Lys—

—Glu—Val—Thr—Val—Gly—)

Cyclo(-Asp—Ile—Lys—Gly—Lys—

—Glu—Val—Thr—Val-β-Ala—)

*R$_2$ as defined above.

Polymeric Peptides Wherein n is an Integer Between 3 and 20

(Asp-Ile-Lys-Gly-Lys-Glu-Val-Thr-Val)$_n$-R$_2$

Selective acylation of Lys side chain NH$_2$ group

The amino-terminal amino group and/or the lysine or threonine side chains may optionally be acylated by formyl, acetyl, propionyl and similar lower alkylacyl residues or by aryl or heterocyclic acyl residues such as benzoyl, thenoyl, nicotinoyl, isonicotinoyl, n-alkylnicotinoyl and their dihydro and tetrahydro derivatives. Such modifications will enhance the blood-brain-barrier permeability of the therapeutic agent. (C.R. Creveling et al, (1969) *Experientia* 25:26-27 and N. Bodor et al. (1981) *Science* 214:1370-1372.

It should be noted that the above C5 and C2 analogs are representative only and additional modifications can be made to other positions in accordance with the present invention.

C. Preparation Methods

The peptides of the present invention may be synthesized by any techniques that are known to those skilled in the peptide art. An excellent summary of the many techniques so available may be found in J.M. Stewart and J.D. Young, *Solid Phase Peptide Synthesis*, 2nd Ed., Pierce Chemical Co., Rockford, Ill. (1984) and G. Barany and R.B. Merrifield, *The Peptides: Analysis, Synthesis, Biology,* Editors E. Gross and J. Meienhofer, Vol. 2, Academic Press, New York (1980), pp. 3-254, for solid phase peptide synthesis; and M. Bodansky, *Principles of Peptide Synthesis,* Springer-Verlag, Berlin (1984) and E. Gross and J. Meienhofer, Eds., *The Peptides: Analysis, Synthesis, Biology, supra,* Vol. 1, for classical solution synthesis.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

Typical protecting groups include t-butyloxycarbonyl (Boc), 9-fluorenylmethoxycarbonyl (Fmoc) benzyloxycarbonyl (Cbz); p-toluenesulfonyl (Ts); 2,4-dinitrophenyl; benzyl (Bzl); biphenylisopropyloxycarboxycarbonyl, t-amyloxycarbonyl, isobornyloxycarbonyl, o-bromobenzyloxycarbonyl, cyclohexyl, isopropyl, acetyl, o-nitrophenylsulfonyl and the like. Of these, Boc is preferred.

Typical solid supports are generally classified as cross-linked polymeric supports. These can include divinylbenzene cross-linked styrene-based polymers, for example, divinylbenzene-hydroxymethylstyrene copolymers, divinylbenzene-chloromethylstyrene copolymers and divinylbenzene-benzhydrylaminopolystyrene copolymers. The last of these materials, as illustrated herein using p-methyl-benzhydrylamine resin, offers the advantage of directly introducing the terminal amide function into the peptide chain, which function is retained by the chain when the chain is cleaved from the support.

In the preferred practice of the invention, the peptides are prepared by conventional solid phase chemical synthesis on, for example, an Applied Biosystems, Inc. (ABI) 430A peptide synthesizer using a resin which permits the synthesis of the amide peptide form and t-Boc (tert-butyloxycarbonyl) derivatives (Peninsula Laboratories, Inc.) with standard solvents and reagents. Peptide composition is confirmed by quantitative amino acid analysis and the specific sequence of each peptide may be determined by sequence analysis.

Alternatively, peptides containing only natural amino acids can be produced by recombinant DNA techniques by synthesizing DNA encoding the desired peptide, along with an ATG initiation codon. Next the DNA is cloned into an appropriate expression vector, such as pBR322-type vectors, using conventional methods to amplify the DNA. Once the sequence has been suitably amplified, it may be transferred to an appropriate expression vector.

Selection of the particular expression vector depends upon the particular host used. For example, bacterial plasmids are used advantageously with *E. coli* cells. The expression vector preferably includes at least one regulatory element, which enables one to induce and/or suppress the expression of the introduced sequence. Thus, one may grow the host culture to a desired density prior to expressing the desired peptide and harvesting the product. If a fusion protein was produced, cleavage of the desired peptide from the fused protein is also performed.

The peptides may also be produced by enzymatic or chemical cleavage of purified NGF or a polypeptide having the desired sequence. Such procedures are conventional and well known in the art.

The original source for the derivation of the present peptides is NGF. However, a search through the library of peptide sequences (400,000 amino acid residues) collected by the National Biomedical Research Foundation (George Washington University Medical Center, Washington, D.C.) demonstrated 22 peptides which contain KGKE (peptide C5). Of the 22 peptides found, 12 occur in eukaryotic cells as shown in Table 2 below. Thus, while the NGF-derived peptides have certain agonist or antagonist properties for NGF, they may also find utility as agonists or antagonists to one or more of the peptides described below.

TABLE 2

| Peptides Containing KGKE |
|---|
| Apolipoprotein B-100 precursor - Human |
| Carbonic anhydrase III - Human, horse |
| Hypothetical polymerase - Fruit fly transposable element 17.6 |
| Platelet basic protein - Human |
| Heat shock protein 26 - Fruit fly |
| 5-aminolevulinate synthase precursor - Chicken |
| Gene PET494 protein - Yeast |
| Adenylate cyclase - Yeast |
| DNA-directed RNA polymerase II - Yeast, fruit fly |
| 40S ribosomal protein S14 - Chinese hamster |
| Connective-tissue activating peptide III - Human |
| pol-like polyprotein - Fruit fly |

After synthesis, the peptides of the present invention may then be assayed to determine their activity in the NGF bioassay using dissociated embryonic chick dorsal root ganglia neurons according to published procedures, such as, for example, Riopelle et al, (1981) *J Neurobiol* 12:175-186 or Varon et al (1981) *Dev Brain Res* 1:73-87. Any peptide of interest may be evaluated in this assay to determine whether the peptide possesses antagonist or agonist activity with respect to NGF. If the peptide of interest is capable of inhibiting neuronal attachment, survival or neurite outgrowth in the presence of NGF, the peptide is defined as an antagonist. Similarly, if the peptide is capable of supporting neuronal attachment, survival or neurite outgrowth in the absence of NGF, it is defined as an agonist.

The versatility of this assay provides a convenient tool to assess whether a specific peptide of interest falls within the scope of the present invention. It should be understood that while particular species may or may not have utility as an agonist or antagonist, all are useful in the development of organic agonists and antagonists since lack of activity is important to understanding and defining the NGF binding site. Thus, additional peptides may be generated from other regions within NGF, including peptides containing amino acid substitutions or deletions, as well as other chemical modifications, which may lead to peptides with greater inhibitory activity or perhaps a more significant agonist effect as measured in the NGF bioassay. Other variations and modifications will be apparent to those of ordinary skill in the art, and are to be considered within the scope of the instant invention.

D. General Methods of Use

The peptides described herein can be used to treat, a number of neurodegenerative or neoplastic disorders. Alzheimer's disease is a neurodegenerative disorder. One of the hallmarks of Alzheimer's disease is the presence of numerous neuritic plaques. These plaques consist of degenerating axons and neurites surrounding an amyloid plaque core composed of 5- to 10-nm proteinaceous filaments. Similar filaments are also found outside of plaques as cerebrovascular amyloid. The brains of aged individuals with Down's syndrome also have both types of amyloid deposits. The β-protein is the principal protein component found in both cerebrovascular and neuritic plaque amyloid. A common mechanism may thus underlie the formation of amyloid in these diseases.

As demonstrated herein, NGF is shown to promote the expression of the genes for both the β-protein and the prion protein. An isoform of the latter protein is the infectious agent causing scrapie and is chemically related to the infectious agent(s) causing Creutzfeldt-Jacob disease, kuru, and to the hostgene product causing Gerstmann-Straussler syndrome. Individuals suffering from these disorders or having a predisposition to these disorders may be treated with the NGF antagonist peptides of the invention to regulate the expression of these genes and their proteins, and therefore reduce the accumulation of the β-protein in Alzheimer's disease and Down's syndrome or the prior protein in CJD, kuru and GSS.

The agonist peptides of the present invention may also be used to treat neurodegenerative disorders caused by a lack of NGF, such as, for example, Huntington's disease. In this disease, cholinergic neurons in the caudate-putamendegenerate. As NGF has been shown to support the differentiation of cholinergic neurons, agonist peptides may be administered to enhance the activity of the cholinergic neurons present in the caudate-putamen.

Analogs of NGF fragments with NGF activity as described above have potentialpharmaceutical applications in situations involving nerve damage from traumatic accidents, stroke and encephalitis.

The peptides of the invention may be administered by parenteral means, including subcutaneous and intramuscular injection, injection into the CNS, implantation of sustained-release depots, intravenous injection, intranasal administration, and the like. Because the present peptides have the potential of being metabolically stable and of crossing the blood-brain barrier, they have the potential of being administered orally or by intravenous injection.

The NGF peptides may be administered as a pharmaceutical composition comprising the peptide in combination with a pharmaceutically acceptable excipient. Such compositions may be aqueous solutions, emulsions, suspensions, gels, liposomal suspensions, and the like. Thus, suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, and the like. One may additionally include suitable preservatives, stabilizers, antioxidants, antimicrobials, buffering agents and the like. A thorough discussion of pharmaceutically acceptable excipients is available in *Remington's Pharmaceutical Sciences*, 2nd Ed., Mack Publishing Co.

Alternatively, one may incorporate or encapsulate the NGF peptides in a suitable polymer matrix, liposome or membrane, thus providing a sustained-release delivery device suitable for implantation near the site to be treated locally. In general, with sustained release delivery, the formulations are constructed so as to achieve a constant concentration which will be bioequivalent to about 100 times the serum level of NGF or 10 times the tissue concentration.

The amount of the peptide required to treat any particular neural disorder will of course vary depending upon the nature and severity of the disorder, the age and condition of the subject, and other factors readily determined by one of ordinary skill in the art. Suitable dosages are from 10 ug/kg to 1000 mg/kg, more preferably 10 mg/kg to 400 mg/kg.

As appreciated by one skilled in the art, the concentration of the formulation for NGF antagonists is generally 10-fold higher, regardless of the mode of administration. The higher dosage assures that the NGF inhibitor is able to compete effectively with endogenously produced NGF.

The following examples are presented in further illustration, but not limitation, of the invention.

EXAMPLES

NGF Peptides

A. Preparation of NGF

NGF was purified from male mouse submaxillary gland and characterized as previously described (Mobley et al, (1976) *Biochem* 15(25):5543–5551).

B. Synthesis and Purification of Peptides

Amide-form peptides were synthesized corresponding to subregions of the NGF molecule. These peptides are listed in Table 3 and are found in regions corresponding to residues 28–38, 66–75 and 98–106. It was speculated that the region from residues 28–38, 66–75 and 98–106, are directly involved in receptor interaction because of their relatively high degree of hydrophilicity, cross-species conservation, and in the case of Regions A and C, the probability of containing a β-turn. Therefore, a synthetic peptide modeled from these regions might serve as an NGF antagonist or agonist. The peptides shown in Table 3 were prepared on an ABI 430A peptide synthesizer using 0.5 millimoles of p-methyl-benzhydrylamine resin (ABI) and Boc amino acid derivatives (Peninsula Laboratories, San Carlos, Calif.) with standard solvents and reagents. Peptides were cleaved from their resins with anhydrous hydrogen fluoride in the presence of anisole and dimethylsulfide at 0° C. Cleaved peptides were washed with ether (3×50 ml), extracted with 10% acetic acid, lyophilized, redissolved in 10 ml purified H$_2$O and lyophilized. The C-terminus of the peptides thus produced ended with an amide. Peptides were purified by high pressure liquid chromatography using either: (1) a C18 uBondapak column (Waters and Co.), eluted with a linear gradient of acetonitrile in 0.1% trifluoroacetic acid; and/or (2) a polysulfoethyl A cation exchange column (Poly-LC, Columbia, Md.) employing a gradient of 20 to 500 mM ammonium acetate in 25% acetonitrile, pH 6.8. The central portions of the major peak (230 nm) from each of several runs were combined. An aliquot was reapplied to the column under the same conditions. The analytical runs showed no detectable impurities. Peptide composition was confirmed by quantitative amino acid analysis. The sequence of peptide C5 (KGKE) was determined via automated Edman degradation.

TABLE 3

Activity of NGF Peptides

| Putative Receptor Binding Domain Region | | $IC_{50}$** ($\mu$moles/ml) Antagonist Activity | Lowest Concentration for Detected Agonist Activity ($\mu$moles/ml) |
|---|---|---|---|
| C1 | ATDIKGKEVTV-NH$_2$ | >0.500 | ND* |
| C2 | DIKGKEVTV-NH$_2$ | >0.500 | 0.500 |
| C3 | KGKEVTV-NH$_2$ | 0.450 | NA |
| C4 | DIKGKE-NH$_2$ | 0.500 | ND |
| C5 | KGKE-NH$_2$ | 0.095 | ND |
| C6 | DIKG-NH$_2$ | 0.300 | ND |
| C7 | KGK-NH$_2$ | 0.125 | ND |
| C8 | IKG-NH$_2$ | 1.060 | ND |
| C9 | IKGK-NH$_2$ | 0.710 | ND |
| C10 | ATDIKG-NH$_2$ | >1.0 | ND |
| C12 | GKE-NH$_2$ | ND | ND |
| C13 | KG-NH$_2$ | ND | ND |
| A1 | SGCRGIDSKH-NH$_2$ | >1.000 | ND |
| A2 | RGIDSKH-NH$_2$ | >1.000 | ND |
| A3 | RGIDS-NH$_2$ | ND | ND |
| A4 | RGIDSK-NH$_2$ | ND | ND |
| B1 | AWRFIRIDT-NH$_2$ | 1.150 | ND |
| B2 | RIDT-NH$_2$ | 0.700 | ND |
| B3 | RFIRIDT-NH$_2$ | ND | ND |
| B4 | RFIRID-NH$_2$ | ND | ND |
| Retest Values | | | |
| C1 | | 1.100 | ND |
| C2 | | 1.100 | 0.500 |
| C3 | | ND | 1.000 |
| C5 | | 0.200 | ND |

*ND = Not determined
NA = No activity up to .500 concentration
**$IC_{50}$ = Concentration at which 50% reduction in neurite-bearing neurons is observed.

C. Bioassay With Dorsal Root Ganglia Neurons

NGF bioassays using dissociated embryonic chick dorsal root ganglia neurons have been described (Varon et al, (1981) *Dev Brain Res* 1:73-87); Riopelle et al, (1981) *J Neurobiol* 12:175-186). Approximately 30 dorsal root ganglia were dissected from each developmental day 8 chick embryo. Ganglia were incubated for 10 min at 37° C. in 5 ml of calcium-magnesium free balanced salt solution (CMF) and then for an additional 10 min in 0.01% trypsin in CMF. Ganglia were then washed twice with 5 ml 10% fetal calf serum in HAMS F-12 medium supplemented with Hanks balanced salt solution (culture medium) and dissociated in 1.5 ml culture medium by trituration (10-15 times) through a flamed glass pipet. The resulting cell suspension was diluted to 10 ml in culture medium, added to a 100 mm culture dish and incubated for 2 hours at 37° C. in 7% $CO_2$—93% air. During this incubation, non-neurons more readily attach to the substratum; therefore, the resulting supernatant contained a relatively enriched neuronal population (80-90% neurons). Each ganglion yielded 15,000-20,000 neurons; more than 95% of which excluded trypan blue.

Tissue culture wells (96 well tissue culture plates, A/2 Costar) were precoated with 0.1 mg/ml of polyornithine for 1-2 hours and then washed twice with 100 ul of sterile water. To each well was added 25 $\mu$l of NGF and 25 $\mu$l of peptide, each in various dilutions (as indicated in FIGS. 1B, 2 and 3) of culture media and 50 $\mu$l of a cell suspension diluted with culture media to a density of 100,000 cells/ml (5000 cells/well). In a second experiment, 2 g/ml of polyornithine were used to coat the wells, and 12.5 $\mu$l each of NGF and the peptide to be tested were added. Additionally, 25 $\mu$l of the diluted cell suspension at the same density (e.g., 100,000 cells/ml (2500 cells/well)) were added.

Figure 1A:
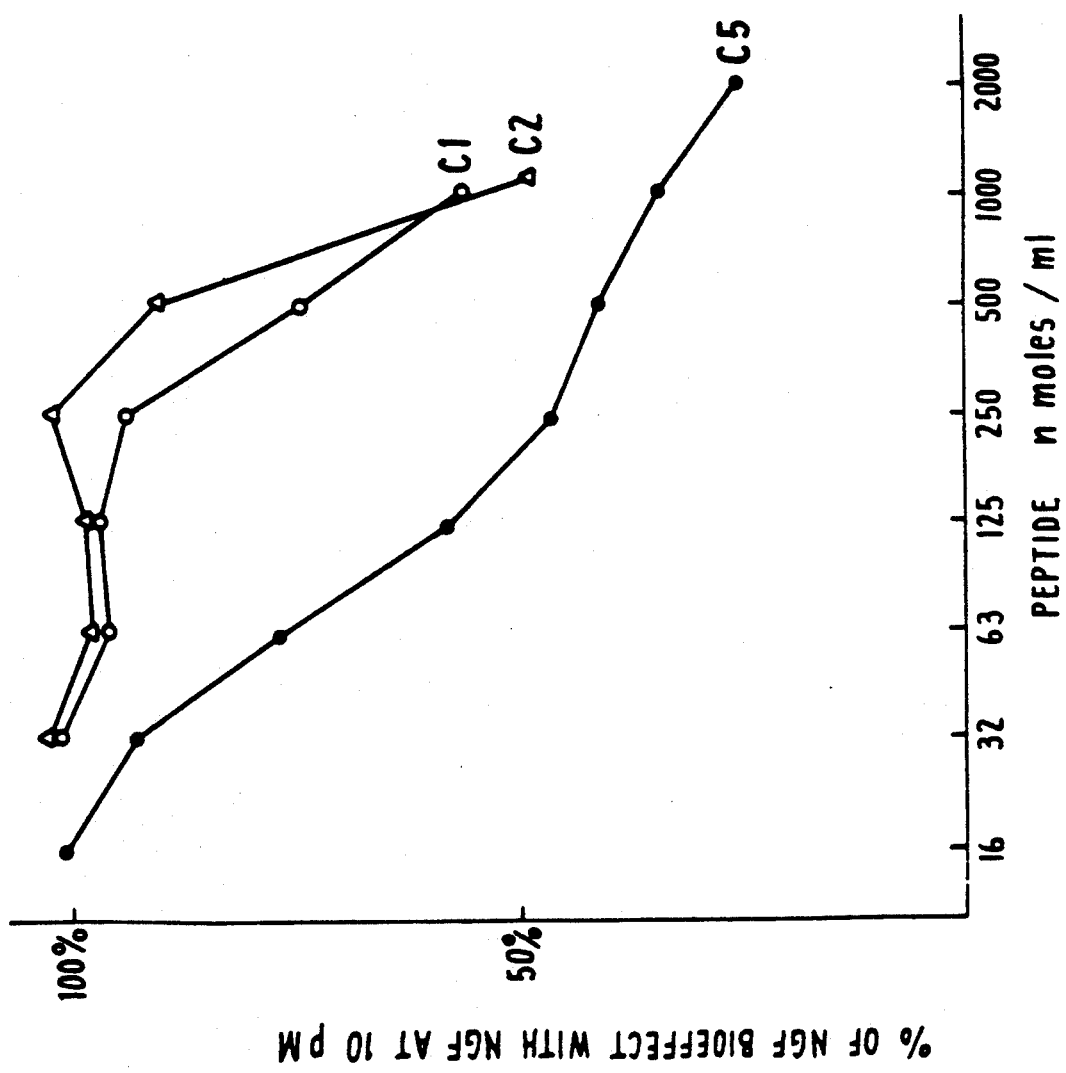

The results obtained were similar in each experiment; FIG. 1A represents the data obtained from the second experiment. Cultures were incubated for 24 hr at 37° C. in 93% air - 7% $CO_2$. Neurite outgrowth was assessed by phase contrast microscopy. The number of neurite-bearing cells in a fixed area of the well was counted. In selected cultures, neuronal survival may be assessed by the addition of MTT (3-(4,5-dimethylthiazol-2-yl)-2,5-diphenyl tetrazolium bromide, Sigma, St. Louis). Blue cellular staining is indicative of ongoing mitochondrial function. Maximum neurite outgrowth was obtained at approximately 800 pg/ml NGF.

Table 3 provides the results for the individual peptides that were tested for agonist or antagonist potential. As observed from the results, peptides from each of the three putative receptor binding domains exhibited some degree of antagonist activity.

The concentration of peptide causing a 50% reduction in the number of neurite-bearing neurons ($IC_{50}$) was determined as shown in Table 3. The inhibition of neurite outgrowth in the presence of C5, C1, or C2 supported by a fixed concentration of NGF, is shown in FIG. 1A. As shown therein, the number of neurite-bearing neurons was reduced with C1 and C2 but to a lesser extent than that observed for C5.

As demonstrated in FIG. 1B, the blocking effect of C5 could be completely overcome by increased concentrations of NGF. The parallel displacement of the dose-response curve suggests that the inhibition by C5 is competitive. The equilibrium dissociation constant for C5 was determined from the formula for antagonist inhibition of agonist stimulation (Furchgott, (1967) *Ann NY Acad Sci* 139:553-570): $K_i = B/((A'/A) - 1)$ where B is the concentration of C5 and A' and A are the $EC_{50}$ values of the agonist dose response curves in the presence and absence of C5. The $K_i$ for C5 was calculated at 47.8 $\mu$M.

Potential nonspecific toxicity of peptide C5 (KGKE) was investigated with embryologic day 10 dorsal root ganglia neurons which also extend neurites in the presence of ciliary neurotrophic factor (CNTF) The effect of peptide C5 on NGF-independent neurite outgrowth was assessed.

C5 (up to 2.6 $\mu$moles/ml) had no detectable effect on the number of embryologic day 10 dorsal root ganglia neurons bearing neurites in response to CNTF (FIG. 3).

D. Support of Neuronal Survival by Synthetic Peptides

Neurons were cultured in the presence of peptides without NGF. Peptide C2 demonstrated neurite-promoting activity. As shown in FIG. 2, the trophic effect of C2 was not equal to NGF at 1 $\mu$moles/ml; C2 elicited only 35% of the effect produced by NGF.

E. Resistance to Proteolysis

The resistance of peptide C5 to proteolytic cleavage during cell culture was assessed. Quadruplicate wells were prepared each containing 2.0 μmole/ml of peptide in culture medium, 100 pg/ml NGF and cells as described above. After 24 hr in culture, 320 ul (4 wells×80 ul) of culture medium were collected. Fresh culture medium containing 2.0 μmole/ml of peptide was also prepared. Both samples of peptide-containing medium were filtered through a Centricon membrane (Amicon, Bedford) with a molecular weight cutoff of 10,000. 250 μl of filtrate was loaded onto a C18 uBondapak analytic HPLC column and run under the same conditions described above for peptide purification. The quantity of peptides in fresh compared to post-culture medium was determined by integration of their absorbance peaks. After 24 hr in culture, more than 80-85% of the initial quantity of peptide C5 was recovered..

F. Ligand Binding Assays

NGF was radiolabeled with $^{125}$I to a specific radioactivity of 40–60 cpm/pg using lactoperoxidase (Sutter et al, (1979) *J Biol Chem* 254:5972-5982). The radioactivity was greater than 90% precipitable in 10% TCA. In preliminary experiments, binding of $^{125}$I-NGF at 37° C. reached a maximum at 30–45 min.

The direct binding assay for $^{125}$I-NGF has been described by Sutter et al (1979, supra) and is incorporated herein by reference. Steady state binding was determined in incubations of dorsal root ganglia cells and $^{125}$I-NGF in PBS containing serum albumin (1 mg/ml) at 37° C. for 60 min. Bound and free $^{125}$I-NGF were separated by centrifugation of the incubation mixture for 2 min at 10,000×g. After the supernatant was aspirated the tips of the incubation tubes were cut and counted in a Beckman 300 Gamma counter.

FIG. 4 demonstrates that at a concentration of 1000 nmoles/ml (n=8), and 2000 nmoles/ml (n=4) peptide C5 produced no change in the specific binding of $^{125}$I-NGF at 10 pM.

NGF Regulation of Gene Expression

A. Tissue Preparation

The birth of hamster litters was recorded as day zero. Hamsters were sacrificed at various postnatal ages and several brain regions were quickly dissected. The regions sampled included septum (basal forebrain), caudate-putamen, thalamus, hippocampus, frontolateral neocortex, and brainstem. Dissections were performed as described (Johnston et al, (1987) *Neurochem Res* 12:985-994). Subiculum was included with hippocampus. Caudal midbrain plus pons constituted the brainstem. For prenatal determinations, a timed-pregnancy animal was anesthetized with Nembutal (15 mg, i.p.) and individual embryos were removed and dissected. Whole forebrain was taken in place of frontolateral neocortex in prenatal animals. ChAT activity was determined in selected tissues as described (Mobley et al, (1985) *Science* 229:284-287).

B. NGF Preparation and Treatment

NGF was prepared by ion-exchange chromatography and characterized as described in the first example. In experiments in which multiple injections were given, NGF (30 μg) was administered intraventricularly (Mobley et al, (1985) supra) on postnatal day (PD) 3, 5 and 7 and sacrifice was on PD 9. Vehicle-injected animals served as controls. In experiments in which a single injection was given, NGF (30 μg) was administered intraventricularly on PD 7 and animals were sacrificed on PD 9. Controls included animals treated with NGF (30 μg) denatured by reduction and carbamoylmethylation (Morris et al, (1971) *Neurobiology* 1:64-67), or injection vehicle alone.

C. RNA Preparation and Blotting

Total RNA was prepared as taught in Kitaguchi et al, (1988) *Nature* 331:530-532). For slot hybridization, RNA samples (5 μg) were ethanol precipitated, vacuum dried, dissolved in 50 μl sterile water and incubated with 150 μl of 6.1 M formaldehyde in 10×SSC at 65° C. for 15 min. Nitrocellulose (BA 85; Schleicher and Schuell) was prewetted with 10×SSC and placed on a slot minifold apparatus (Schleicher and Schuell). Samples were loaded and vacuum applied (Kafatos et al, (1979) *Nucl Acid Res* 7:1541-1552). Filters were baked at 80° C. for 2 hr. The DNA insert of pHaPrP (Oesch et al, (1985) *Cell* 40:735-746) was excised with BamHI (Boehringer-Mannheim) and isolated by preparative gel electrophoresis.

The recovered fragment was labeled to a specific activity of $10^9$ dpm/μg using random priming oligonucleotides (P.L. Biochemicals) and the Klenow fragment (Boehringer-Mannheim). Prehybridization and hybridization of the filters were performed using conventional procedures. Hybridizations were carried out for 16 hr at 42° C. in 3×SSC, 50% formamide, 0.05 M HEPES (pH 7.4), 0.2 mg/ml salmon sperm DNA, 0.15 mg/ml yeast RNA, 0.02% bovine serum albumin, and 0.02% polyvinyl pyrrolidone. Filters were washed in 0.1×SSC, 0.1% SDS at 60° C. for 3 hr and autoradiographed for 1-3 days at −70° C. using Dupont Cronex intensifying screens and Kodak XAR-5 film. Autoradiograms were densitometrically scanned (LKB 2202 Ultroscan; 3390 A Hewlett-Packard integrator) to assess the amount of prion protein (PrP) or β-amyloid precursor protein (BAPP) mRNA. Measurements were accepted when they fell in the range through which signal intensity was linearly related to the amount of RNA loaded.

In examining the developmental time course for PrP gene expression, the tissues of 4 animals were pooled for the prenatal measurement of forebrain PrP mRNA; 7 animals were pooled for brainstem. For each postnatal sample, RNA was prepared from pooled brain regions of entire hamster litters or from 3 to 5 adults. To examine the postnatal ontogenesis of β-amyloid precursor protein mRNA, RNA was prepared as indicated above and two separate samples were examined at each postnatal age.

The relative levels of PrP mRNA in several brain regions was determined in the adult. Individual samples (n=2 for each) were compared to a standard curve prepared by blotting known amounts of PrP cDNA. The cDNA insert of pHaPrP was ethanol precipitated, the pellets dried and resuspended in 400 μl of TE buffer. Serial 10-fold dilutions were then prepared. After the addition of one-tenth volume 3 N NaOH, the dilutions were incubated at 65° C. for 30 chilled, and following the addition of 400 μl of 2 M ammonium acetate, were loaded under vacuum onto nitrocellulose prewetted with 1 M ammonium acetate (Kafatos et al, (1979) supra). Filters were hybridized as described above.

For Northern blotting analysis, RNA samples were ethanol precipitated, washed once with 70% ethanol, and dissolved in 50% formamide, 2.2M formaldehyde. After the addition of one-fifth volume of 10% Ficoll with 1% bromphenol blue, samples were electrophoresed through 1% agarose. The running buffer was 20 mM MOPs (pH 7.0), 1 mM EDTA, 2.2M formaldehyde. After electrophoresis, gels were soaked in 20×SSC and the RNA transferred to nitrocellulose as described (Thomas, (1980) *Proc Natl Acad Sci USA* 72:5201-5205). Filters were prehybridized and hybridized as indicated above.

D. Prion Protein Measurement

PrP levels were measured in the septum of NGF-and vehicle-injected hamsters following a single treatment on PD7. Each tissue sample (the septum of an individual animal) was weighed and then disrupted by trituration through a Pasteur pipette in cold Tris-NaCl-EDTA buffer containing 0.15% NP40 and 0.15% DOC. Extraction was performed on ice for 5 min; cell debris was pelleted 2,000×g for 5 min and proteins were precipitated in 80% methanol at −20° C. for 24 hr. Electrophoresis was performed in 12% polyacrylamide gels according to the method of Laemmli (Laemmli, (1970) *Nature* 227:680-685). Proteins were electroblotted to nitrocellulose filter paper (Towbin et al, (1979) *Proc Natl Acad Sci USA* 76:4350-4354). The filter was blocked with Blotto (5% nonfat-dry milk in PBS), incubated at room temperature with primary antisera (monoclonal antibody 13A5, raised against hamster PrP, (Barry et al, (1986) *J Infect Dis* 154:518-521), and immunostained with the Protoblot alkaline phosphatase system (Promega Biotech, Madison, Wis.). Nitrocellulose filters were densitometrically scanned to determine the amount of PrP.

Results

Developmental Regulation of PrP Gene Expression

To investigate the regulation of PrP gene expression, PrP mRNA was measured in several regions of the hamster brain during pre- and postnatal development. While PrP mRNA was found in all tissues sampled, its ontogenesis varied regionally. Three developmental patterns for PrP gene expression were found: (i) early expression, observed in brainstem and neocortex; (ii) intermediate expression, seen in hippocampus, thalamus and caudate-putamen; and (iii) delayed expression, found in septum. Low levels of PrP mRNA were detected in the brainstem in the immediate prenatal period, but increased rapidly to near-adult levels during the first postnatal week. PrP gene expression in neocortex was similar to brainstem in its developmental pattern except that greater than adult levels were seen during the second postnatal week. In contrast, there was little or no measurable PrP mRNA in hippocampus, caudate-putamen or thalamus through postnatal day 3. By 6 days PrP mRNA had increased. At this time PrP mRNA was 40% of adult levels in hippocampus, 97% in thalamus and 124% in caudate-putamen. PrP mRNA rose to adult or greater than adult levels in all three regions over the next two weeks. In caudate-putamen levels 220% of those in the adult were found at PD 16. Individual brain regions also differed in the amount of PrP mRNA found in adult animals. Randomly selected postnatal RNA samples were also analyzed by Northern analysis. In all instances the hybridizing species migrated as a 2.1 kb band.

Septum was clearly delayed in its expression of PrP mRNA. Not until 9 days of age was PrP mRNA detected in this tissue; 17% of the adult level was measured at this time. PrP mRNA levels rose to 60-70% of adult values by 12 days of age and reached maximal values by PD 16. The delayed appearance of PrP mRNA in septum exhibited a pattern reminiscent of the time-course followed by septo-hippocampal cholinergic markers in the rat (Large et al, (1986) *Science* 234:352-355; Shelton et al, (1979) *Brain Res* 163:263-275). To determine if cholinergic markers followed the same pattern in the hamster, we measured the activity of ChAT, the enzyme which catalyzes the final step of acetylcholine synthesis and is selectively localized in cholinergic neurons. ChAT activity was measured at intervals during postnatal development and the data were compared to those for PrP mRNA. ChAT specific activity in septum was less than 20% of adult levels at PD 3 and remained low through 9 days of age rising to adult levels over the ensuing week. From PD 9 through 16, the developmental increase in ChAT activity in the septum was virtually coincident with that for PrP mRNA. Thus, increasing PrP gene expression in the developing hamster septum was temporally coincident with the differentiation of cholinergic neurons.

NGF Effects on PrP Gene Expression

The coincident rises of ChAT activity and PrP mRNA raised the possibility that these markers were under coordinate control during the development of septal cholinergic neurons. One approach to defining the relationship between PrP gene expression and the development of cholinergic neurons was suggested by prior studies with NGF. In rat brain, NGF injections selectively increased septal ChAT activity but had no effect on glutamic acid decarboxylase or tyrosine hydroxylase, neurotransmitter enzyme markers for GABA-ergic and catecholaminergic neurons, respectively. Moreover, NGF receptors in the rat septum are localized to neuronal cell bodies which in their size and distribution closely resemble cholinergic neurons. Selectivity of NGF action thereby provided a means for examining neuro-chemical events in developing cholinergic neurons. To determine whether or not NGF influences the expression of PrP mRNA, NGF (30 μg) was administered intraventricularly to neonatal hamsters on PD 3, 5, and 7 and the animals were sacrificed on PD 9. Control littermates received injection vehicle alone. In normal animals, ChAT activity at day 9 was 34% of adult levels and PrP mRNA was 17% of adult levels. Similar values were found in vehicle-injected animals. In NGF-treated animals, ChAT activity was increased almost two-fold (FIG. 5A), indicating that hamster basal forebrain cholinergic neurons responded to NGF injection. NGF induced a much larger change in PrP mRNA. The level of septal PrP mRNA was increased approximately 10-fold relative to controls and exceeded the levels found in adults.

In a prior study, we found that a single injection of NGF elicited an increase in the neurochemical differentiation of developing forebrain cholinergic neurons. The NGF-mediated stimulation of ChAT activity in the septum of rat neonates was first evident 48 hr after a single intraventricular injection and persisted for the next several days (Johnston et al, (1987) supra). To determine whether or not an effect of NGF on PrP mRNA would be demonstrable over this time course, NGF was given as a single (30 μg) injection to neonatal hamsters at day 7 and animals were sacrificed 48 hours later, on day 9. Septal ChAT activity was increased 100% relative to vehicle-injected animals [mean±-SEM; vehicle-injected=22.3±1.3 nmol acetylcholine (ACh) formed/hr/mg protein (n=4); NGF=44.0±5.0 (n=4); P<0.005, Student's t-test]; PrP mRNA levels were increased nearly 9-fold (FIG. 5B). Northern blot analysis showed that the PrP mRNA induced by NGF treatment migrated identically to that found in vehicle-injected animals and adults (FIG. 5C). No increase in ChAT activity or PrP mRNA was produced by injection of NGF denatured by reduction and carbamoyl-methylation.

The increase in PrP mRNA induced by NGF treatment was confined to specific brain regions. Of note, the caudate-putamen in the rat contains NGF-responsive cholinergic neurons which are distinct from those found in basal forebrain. A single NGF injection in neonatal hamsters increased ChAT activity in caudate-putamen by approximately 65% [vehicle=56.1±4.5 (n=3); NGF=92.4±6.3 (n=3); P>0.01, Student's t-test]. PrP mRNA was increased by 70% relative to vehicle-injected animals (FIG. 5B). In contrast to the responses in septum and caudate-putamen, NGF had no effect on PrP mRNA levels in thalamus or hippocampus (FIG. 5B).

NGF Effects on the Levels of PrP

NGF effects on basal forebrain neurons produced a far greater increase in PrP mRNA levels than in ChAT activity in either the multiple or single injection protocol. To compare NGF effects on PrP mRNA levels with those for the prion protein, we measured the level of PrP in the septum 48 hr following a single NGF (30 ug) injection given on PD 7. By Western blot analysis there was a 3.3-fold increase in PrP. Thus, under the conditions of this experiment, the NGF-induced increase in the level of the PrP protein was somewhat less marked than the increase in PrP mRNA.

Regulation of β-Protein Precursor (β-PP) Gene Expression in Developing Septum; NGF Effects As was the case for PrP, β-PP mRNA was found in all the brain tissues sampled. The size of the mRNA in septum was 3.5 kb. The pattern for the ontogenesis of β-PP mRNA levels in the septum was similar to that for PrP. β-PP mRNA levels were first detected at PD9 when they equaled 19% of those found in the adult. There was an increase in β-PP mRNA during the next several days such that peak levels (325% of adult) were achieved at PD16.

NGF injection had a marked effect on the level of β-PP mRNA. After a single treatment on PD7, mRNA levels for β-PP were increased 4-fold relative to vehicle-injected animals. As shown in FIG. 6, the effect of NGF was regionally specific in that NGF induced no increase in β-PP in the thalamus.

What is claimed is:

1. A peptide displaying activity in an NGF bioassay using dissociated embryonic chick dorsal root ganglia neurons, wherein said peptide is composed of a contiguous sequence of amino acids found within a region of NGF defined by amino acid residues 26–40 inclusive, or conservative substitutions thereof, numbered in accordance with native, murine NGF, and further wherein said peptide comprises the amino acid sequence KGKE.

2. The peptide of claim 1 wherein said contiguous sequence of amino acids is found within amino acid residues 28–38 of NGF.

3. The peptide of claim 1 wherein the α-carboxyl group of the amino acid residue at the c-terminus is amidated.

4. The peptide of claim 3 wherein said contiguous sequence of amino acids is ATDIKGKEVTV-NH$_2$.

5. The peptide of claim 3 wherein said contiguous sequence of amino acids is DIKGKEVTV-NH$_2$.

6. The peptide of claim 3 wherein said contiguous sequence of amino acids is KGKEVTV-NH$_2$.

7. The peptide of claim 3 wherein said contiguous sequence of amino acids is DIKGKE-NH$_2$.

8. The peptide of claim 3 wherein said contiguous sequence of amino acids is KGKE-NH$_2$.

9. A pharmaceutical composition comprising an effective amount of a peptide displaying NGF activity wherein said peptide is composed of a contiguous sequence of amino acids found within a region of NGF defined by amino acid residues 26–40 inclusive, or conservative substitutions thereof, numbered in accordance with native, murine NGF, and further wherein said peptide comprises the amino acid sequence KGKE; in combination with a pharmaceutically acceptable excipient.

* * * * *